(12) United States Patent
Gerbes et al.

(10) Patent No.: US 8,858,934 B2
(45) Date of Patent: Oct. 14, 2014

(54) METHOD FOR PRODUCING CELLS HAVING CHARACTERISTICS OF HEPATOCYTES

(75) Inventors: Alexander Gerbes, Pullach-Großhesselohe (DE); Andreas Benesic, Munich (DE)

(73) Assignee: ABAG Verwaltungs GmbH, Pullach-Grosshesselohe (DE)

( * ) Notice: Subject to any disclaimer, the term of this patent is extended or adjusted under 35 U.S.C. 154(b) by 0 days.

(21) Appl. No.: 13/816,404

(22) PCT Filed: Aug. 11, 2011

(86) PCT No.: PCT/EP2011/063871
§ 371 (c)(1),
(2), (4) Date: Apr. 16, 2013

(87) PCT Pub. No.: WO2012/020101
PCT Pub. Date: Feb. 16, 2012

(65) Prior Publication Data
US 2013/0195813 A1   Aug. 1, 2013

(30) Foreign Application Priority Data
Aug. 12, 2010   (EP) .................................... 10172639

(51) Int. Cl.
*C12N 5/07* (2010.01)
*C12N 5/071* (2010.01)
*C12N 5/02* (2006.01)

(52) U.S. Cl.
CPC .......... *C12N 5/067* (2013.01); *C12N 2501/119* (2013.01); *C12N 2501/91* (2013.01); *C12N 2501/33* (2013.01); *C12N 2501/2303* (2013.01); *C12N 2501/22* (2013.01); *C12N 2501/335* (2013.01); *C12N 2500/40* (2013.01); *C12N 2506/115* (2013.01); *C12N 2501/11* (2013.01)
USPC ........... 424/93.7; 435/347; 435/370; 435/386

(58) Field of Classification Search
None
See application file for complete search history.

(56) References Cited

U.S. PATENT DOCUMENTS

2004/0009595 A1 * 1/2004 Kremer et al. ................ 435/372
2009/0105140 A1 * 4/2009 Rosen et al. .................... 514/12
2010/0143313 A1 * 6/2010 Yarmush et al. ............. 424/93.7

FOREIGN PATENT DOCUMENTS

WO   WO 2009050707 A1 *   4/2009

OTHER PUBLICATIONS

Galle et al. Involvement of the CD95 (APO-1/Fas) Receptor and Ligand in Liver Damage. 1995. Journal of Experimental Medicine, 182:1223-1230. specif. p. 1223.*
Fetal Bovine Serum. Datasheet [online]. Labome.com.The world of laboratories. Copyright 2013 [retrieved on Sep. 30, 2013]. Retrieved from the Internet: <URL: http://www.labome.com/method/Fetal-Bovine-Serum.html>.*
Javitt, *The FASEB Journal*, 4: 161-168 (1990).
Aninat et al., *Drug Metabolism and Disposition*, 24:75-83 (2006).
Cerec et al., *Hepatology*, 45: 957-967 (2007).
Fausto, *Hepatology*, 39 (6): 1477-1487 (2004).
Si-Tayeb et al., *Hepatology*, 51 (1): 297-305 (2010).
Ruhnke et al., *Gastroenterology*, 128 (7): 1774-1786 (2005).
Ruhnke et al., *Transplantation*, 79 (9): 1097-1103 (2005).
Ehnert et al., Drug Metab. Dispos., 36 (9): 1922-1929 (2008).
Riquelme et al., Differentiation, 77 (3): 263-276 (2009).
Bauvois, *Eur. J. Immunol*, 20 (3): 459-68 (1990).
Szasz G: Gamma-glutamyltranspeptidase, in: *Methoden der Enzymatischen Analyse*, 3rd ed., (vol. 1), edited by Bergmeyer HU, Weinheim/Bergstr., Verlag chemie, 757-762 (1974).
Bondar et al., *Clin Chem*, 20/5: 586-590 (1974).
Donato et al., *Drug Metabolism and Disposition*, 32 (7): 699-706 (2004).
Esposito et al., *Kidney Int.*, 58: 123-130 (2000).
Ziyadeh et al., *Am. J. Physiol.*, 259: F704-F714 (1990).
Brown CD, *Toxicol. App. Pharmacol.*, 233 (3): 428-38 (2008).
Lopez et al., *Proc. Natl. Acad. Sci. USA*, 89: 11842-11846 (1992).
Hofer et al., *Physiol. Res.*, 58: 247-252 (2009).
Taylor et al., *J. Biol. Chem.*, 269 (49): 31171-31177 ( 1994).
Gstraunthaler et al., *Cell Physiol. Biochem*, 9 (3): 150-172 (1999).
Wolff et al., *Am. J. Physiol.*, 265 (5): C1266-1270 (1993).
Tuschl et al., *Chem Biol Interact.*, 181 (1): 124-37 (2009).
Elaut et al., *Curr. Drug Metab.*, 7 (6): 629-660 (2006).
Koal and Deigner, *Curr. Mol. Med.*, 10 (2): 216-226 (2010).
Klein et al., *Front. Pharmacol.*, 1: 1-20 (2010).
Kormann et al., *Nat. Biotech*, 29: 154-157 (2011).
Schumann G et al., *Clin Chem Lab Med.*, 40 (7): 718-724 (2002).
Benesic et al., *Kidney Blood Press Res.* 29 (5): 280-293 (2006).
Weiss et al., *J Hepatol.*, 38 (4): 476-482 (2003).

* cited by examiner

*Primary Examiner* — John S Brusca
*Assistant Examiner* — Sharon M Papciak
(74) *Attorney, Agent, or Firm* — Davis Wright Tremaine LLP

(57) ABSTRACT

The present invention relates to a method of producing cells having at least one characteristic of human hepatocytes as well as to cells produced by said method and uses of these cells.

14 Claims, 23 Drawing Sheets

Figure 5a (continued 2)
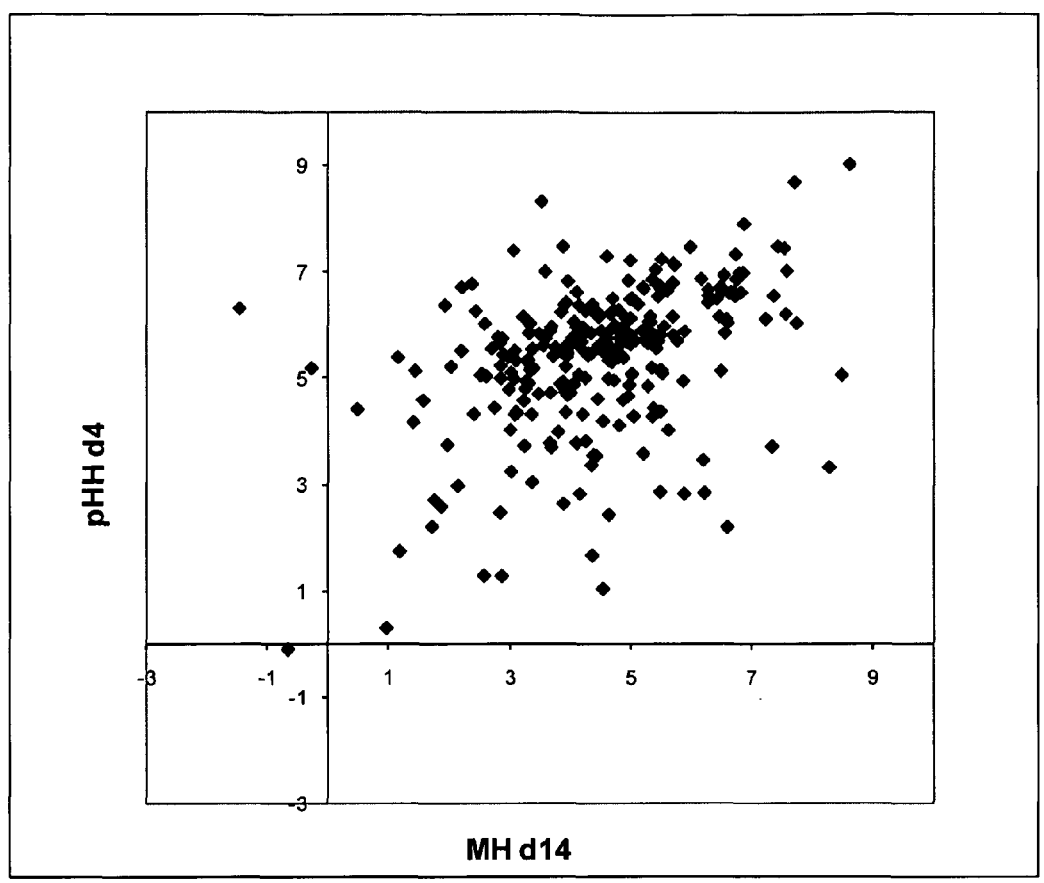

Figure 5b) continued
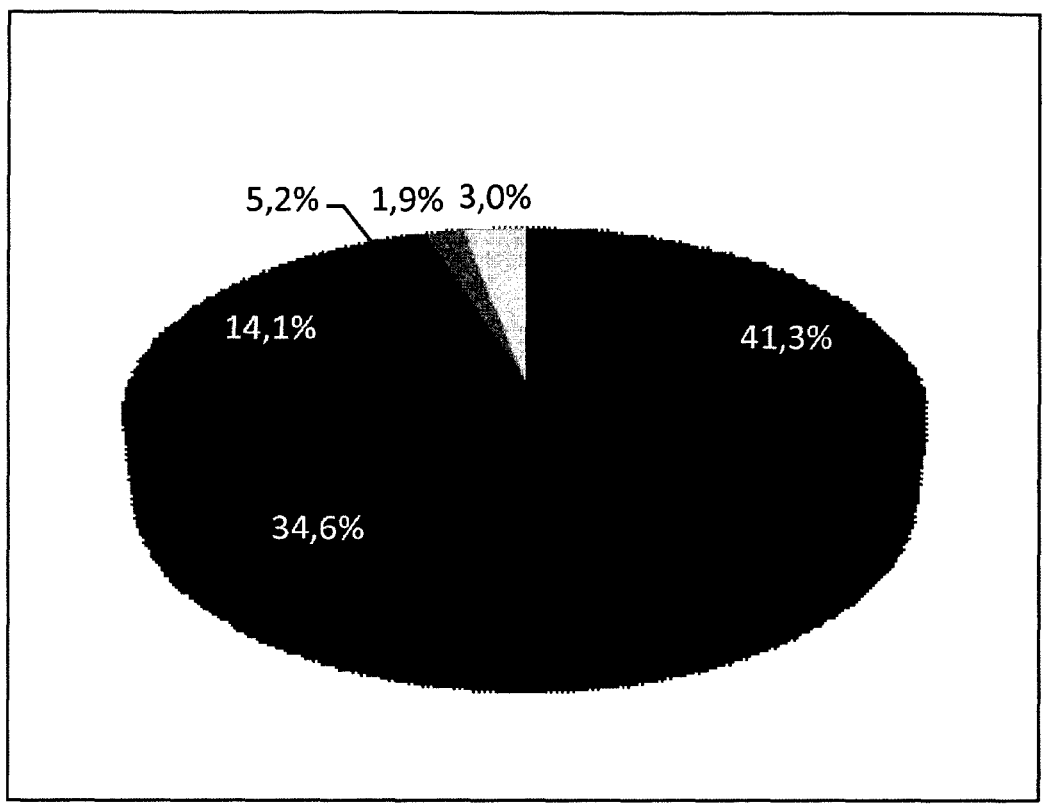

Figure 5b) continued 2
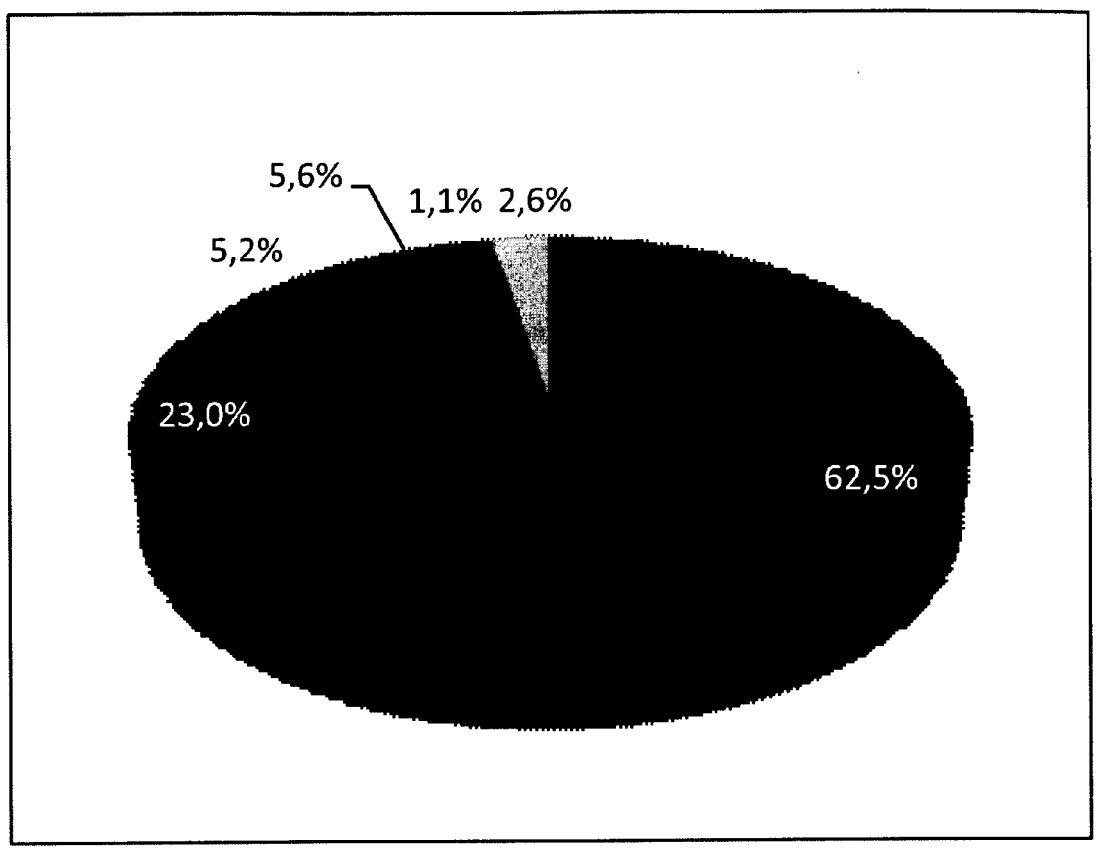

Figure 5c) continued
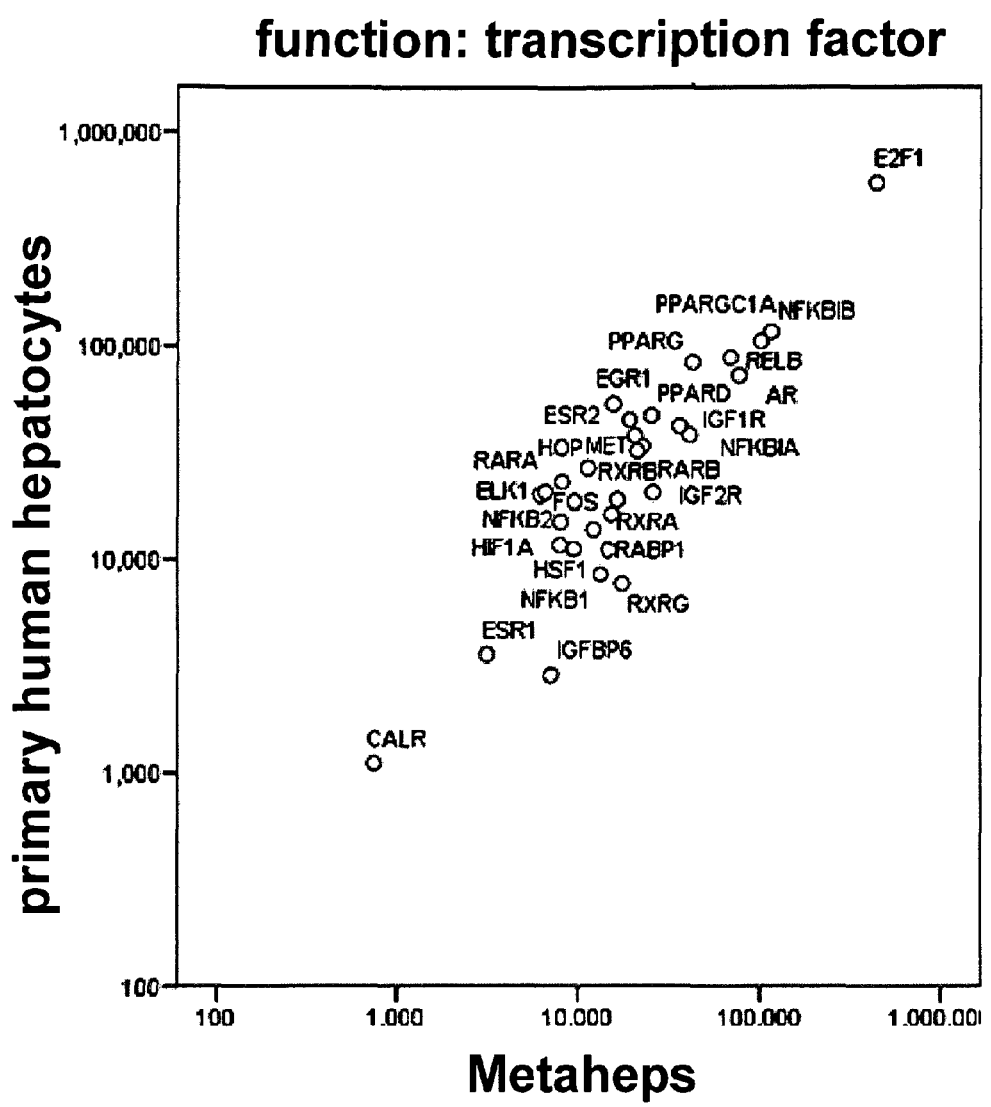

Figure 5c) continued 2
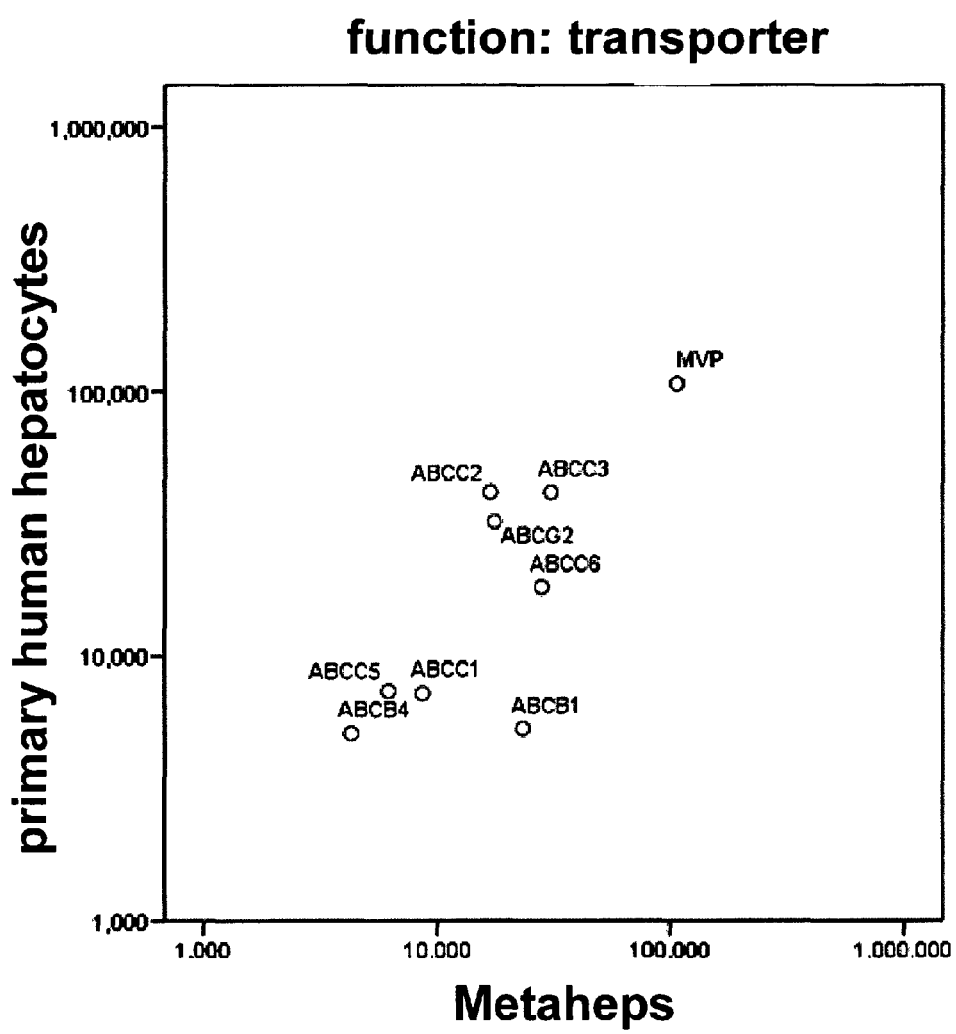

METHOD FOR PRODUCING CELLS HAVING CHARACTERISTICS OF HEPATOCYTES

CROSS-REFERENCE TO RELATED APPLICATIONS

The present application is a U.S. National Stage entry under 35 U.S.C. §371 of International Application No. PCT/EP2011/063871, filed on 12 Aug. 2011, designating the United States of America and published in English on 16 Feb. 2012, which in turn claims priority to European Patent Application No. 10172639.6, filed on 12 Aug. 2010, each of which is hereby incorporated by reference in its entirety.

FIELD OF THE INVENTION

The present invention relates to a method of producing cells having at least one characteristic of human hepatocytes as well as to cells produced by said method and uses of these cells.

BACKGROUND OF THE INVENTION

The liver is an organ with a variety of functions such as glycogen storage, plasma protein synthesis, hormone production and detoxification and is thus necessary for survival. The cells of the main tissue of the liver which are responsible for most of the functions of the liver are called hepatocytes.

Human hepatocytes can be used for example for cell transplantation in acute and chronic liver failure. Furthermore, human hepatocytes are used by the pharmaceutical industry in vitro in pre-clinical drug testing and high throughput screening to determine whether a certain drug will exert deleterious effects on the human body. However, the use of primary hepatocytes is limited by the restricted availability of liver tissue, the early phenotypic changes occurring in cultured primary hepatocytes and their limited life span. Furthermore, primary hepatocytes exhibit large variability in CYP activities and in magnitude of induction after incubation with prototypical inducers. Hence, results obtained with primary hepatocytes may not be reproducible to the extent required for in vitro pre-clinical drug testing.

Efforts have thus been made to develop alternatives to the use of primary hepatocytes. One alternative is the use of immortalized cell lines such as HepG2 and HepaRG cells (Javitt (1990) The FASEB Journal 4: 161-168; Aninat et al. (2006) Drug Metabolism and Disposition 24: 75-83; Cerec et al. (2007) Hepatology 45: 957-967). However, many of these cell lines are of tumorigenic origin and do not retain the normal hepatocellular metabolizing capacities, so that their applicability in pharmacology and toxicology and even more so their applicability in vivo is greatly limited.

Other approaches use adult stem cells from bone marrow or induced pluripotent stem cells which are differentiated to hepatocytes (Fausto (2004) Hepatology 39(6): 1477-1487; Si-Tayeb et al. (2010) Hepatology 51(1): 297-305). However, these approaches require a complex isolation of the starting material and a complex differentiation protocol as well as a manipulation of the genome of these cells.

Finally, cells having characteristics of human hepatocytes, called "neo-hepatocytes", have been obtained from peripheral monocytes by first treating the monocytes with a mixture of 5 ng/ml M-CSF and 0.4 ng/ml IL-3 for six days and subsequently treating the cells with 3 ng/ml FGF-4 for at least seven days (Ruhnke et a. (2005) Gastroenterology 128(7): 1774-1786; Ruhnke et al. (2005) Transplantation 79(9): 1097-1103; Ehnert et al. (2008) Drug Metab. Dispos. 36(9): 1922-1929). However, later it has been shown that these cells most closely resemble a population of serum-deactivated macrophages and it was concluded that although these cells exhibit some phenotypic characteristics of hepatocytes, these characteristics are acquired as part of a normal program of macrophage differentiation (Riquelme et al. (2009) Differentiation 77(3): 263-276). Furthermore, the differentiation protocol leading to "neo-hepatocytes" showed only a low reproducibility.

Hence, there is still a need for a method for producing cells having at least one characteristic of human hepatocytes with high reproducibility and a high cell yield and cells obtained by such a method.

OBJECT AND SUMMARY OF THE INVENTION

It is thus an object of the present invention to provide a method for producing cells having at least one characteristic of human hepatocytes which method is reproducible to a large extent and produces cells with a high yield.

It is a further object of the present invention to provide cells having at least one characteristic of human hepatocytes which cells are suitable for cell transplantation and in vitro drug testing.

These and further objects of the invention, as will become apparent from the description, are attained by the subject-matter of the independent claims.

Some of the preferred embodiments of the present invention form the subject-matter of the dependent claims.

The inventors of the present invention have found that the treatment of human peripheral monocytes with IL-3 and adenosine and subsequently with FGF-4 reproducibly produces cells having characteristics of human hepatocytes with a high cell yield. These cells are capable of undergoing apoptosis when treated with an apoptosis-inducing substance such as CD95 ligand. Furthermore, these cells show long-term expression of cytochrome enzymes and thus allow the determination of not only the acute toxicity, but also of the long-term toxicity of substances in an in vitro test. Furthermore, the inventors were able to show that the cells produced by the method of the present invention show differences in cytochrome expression depending on the gender of the donor of the peripheral monocytes, thus also facilitating investigation of gender-dependent differences in drug metabolism.

Accordingly, in one embodiment, the present invention provides a method for producing cells having at least one characteristic of human hepatocytes, said method comprising the steps of:
(a) seeding human monocytes in a culture vessel in a cell culture medium;
(b) culturing the monocytes in a cell culture medium comprising interleukin 3 (IL-3) and adenosine; and
(c) culturing the cells simultaneously with or subsequent to step (b) in a cell culture medium comprising fibroblast growth factor 4 (FGF-4).

In a preferred embodiment of the present invention the cell culture medium in step (b) further comprises macrophage colony-stimulating factor (M-CSF).

In a further preferred embodiment of the present invention the adenosine is present in the cell culture medium of step (b) in a concentration of 10-300 nM.

In still another preferred embodiment of the present invention, the cell culture medium in step (c) further comprises at least one compound selected from the group consisting of epidermal growth factor (EGF), glucagon, insulin and heparin, and, in an even more preferred embodiment of the present invention, the cell culture medium in step (c) comprises EGF, glucagon, insulin and heparin.

In a further preferred embodiment of the present invention, the cell culture medium in step (a), (b) and/or (c) is serum-free, and, in an even more preferred embodiment, the cell culture medium comprises albumin.

In a further embodiment of the present invention, the method further comprises the step of changing the cell culture medium at a time point less than one hour after seeding the human monocytes.

In still another embodiment of the present invention, the cell culture medium volume in step (b) and/or (c) is 40 to 90 µl/cm$^2$ of the culture vessel.

In one embodiment of the present invention, the cells are cultured in step (b) of the method of the present invention for at least four days.

In still another embodiment of the present invention, the cells are cultured in step (c) of the method of the present invention for at least seven days.

The present invention further provides cells having at least one characteristic of human hepatocytes, which cells are obtainable by the method of the present invention and which can be kept in culture for at least 15 days.

Preferably, hepatocytes isolated from human liver are excluded.

More preferably, the cells are capable of undergoing apoptosis when incubated with a CD95-ligating antibody for 24 hours.

The present invention is further directed to the use of the cells of the present invention for in vitro toxicity studies or in cell therapy.

DETAILED DESCRIPTION OF THE INVENTION

Figure 1A:
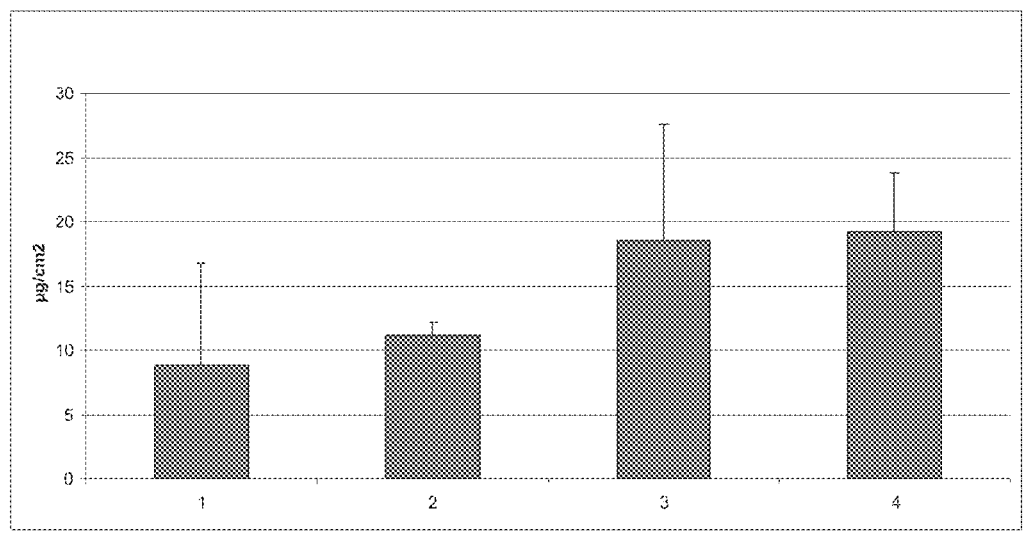
FIG. 1: Influence of different culture conditions on protein content (a) and DPP-IV, γ-GT, ALT and LDH enzyme activities (b) after 14 days of culture of monocytes
- Lane 1: Cells established by the protocol described in Ruhnke et al. (2005) Gastroenterology 128(7): 1774-1786 called "neo-hepatocytes"
- Lane 2: Cells established according to the protocol of Ruhnke et al., but with reduced medium volume (about 70 µl/cm$^2$), shorter adhesion time (about 20 minutes), medium without β-mercaptoethanol, 1 ng/ml IL-3 and 0.5 ng/ml M-CSF
- Lane 3: Conditions as in Lane 2, but with DMEM/Ham's F12 as basal medium, which further comprises 100 nM adenosine in the first culturing step
- Lane 4: Culture conditions as described in Lane 3, wherein the cell culture medium of the second culturing step additionally comprises 10 ng/ml recombinant human EGF, 0.28 IU recombinant human insulin, 5 nM recombinant human glucagon and 5 IU/ml heparin
Figure 1B:
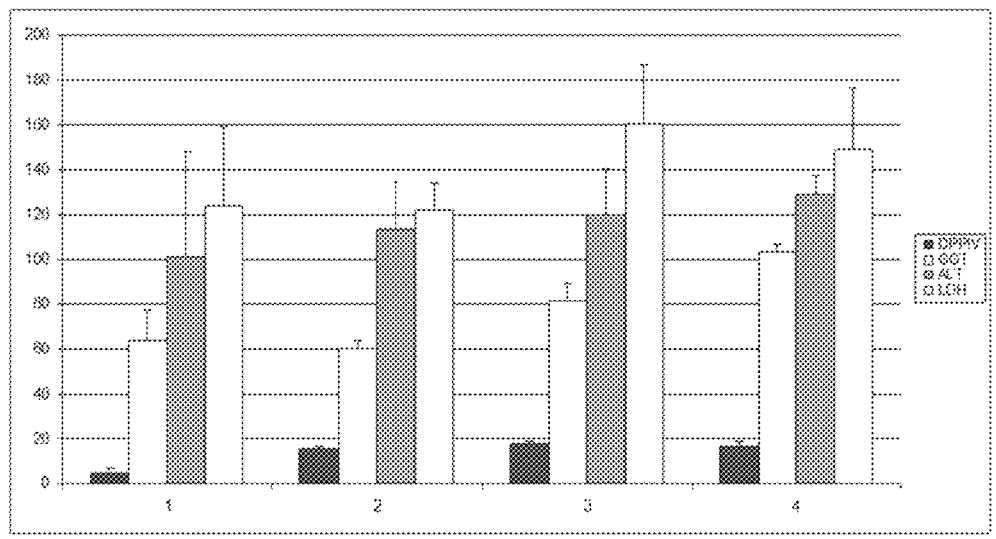
Figure 2A:
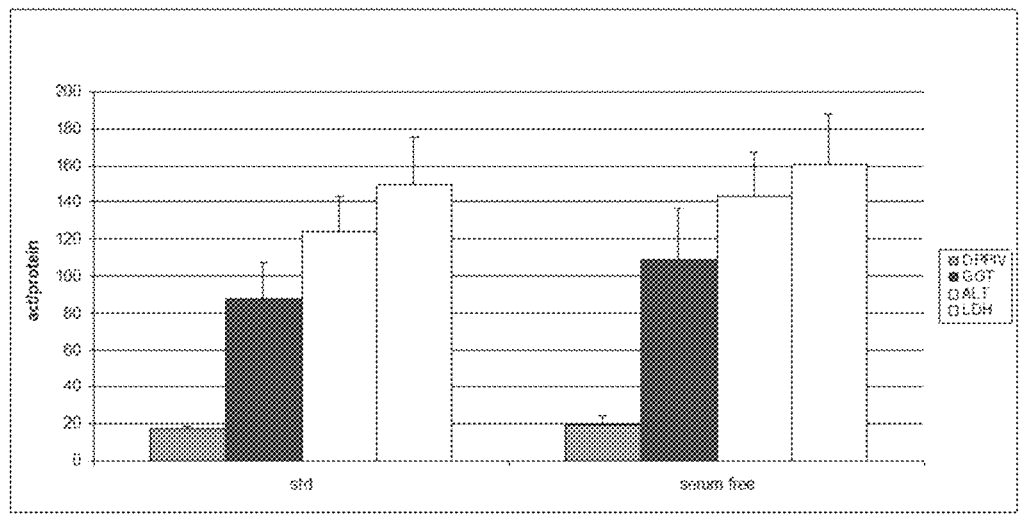
FIG. 2: Influence of serum-free cultivation in 2% human albumin on different hepatocytic characteristics of the cells obtained by the method of the present invention after 14 days of culture of monocytes
- (a) Specific enzyme activities of DPP-IV, γ-GT, ALT and LDH in the cells of the present invention cultured under standard (std; i.e. 10% FCS) and serum-free conditions for the entire culture period, i.e. steps b) and c) of the method of the present invention (n=4 donors)
- (b) APAP toxicity in the cells of the present invention cultured under standard (i.e. 10% FCS) and serum-free conditions and incubated with different concentrations of APAP for 24 hours, as determined by release of LDH as a marker of cell damage (n=4 donors)
- (c) Induction of cytochrome CYP1A2 activity by treatment with 1 µM 3MC (3-methyl cholanthrene) for 48 hours in the cells of the present invention cultured under standard (std; i.e. 10% FCS) and serum-free (HA) conditions (n=3 donors)
- (d) Secretion of Factor VII in response to stimulation with different concentrations of menadione for 48 h in the cells of the present invention cultured under standard (i.e. 10% FCS) and serum-free conditions for different periods
- (e) Urea synthesis in the cells of the present invention cultured for 14 days under standard (i.e. 10% FCS) and serum-free conditions without (control) and with 100 µM NH$_4$Cl for 24 hours
- (f) Morphology of the cells of the present invention cultured under standard (i.e. 10% FCS; upper picture) and serum-free conditions (lower picture)
Figure 2B:
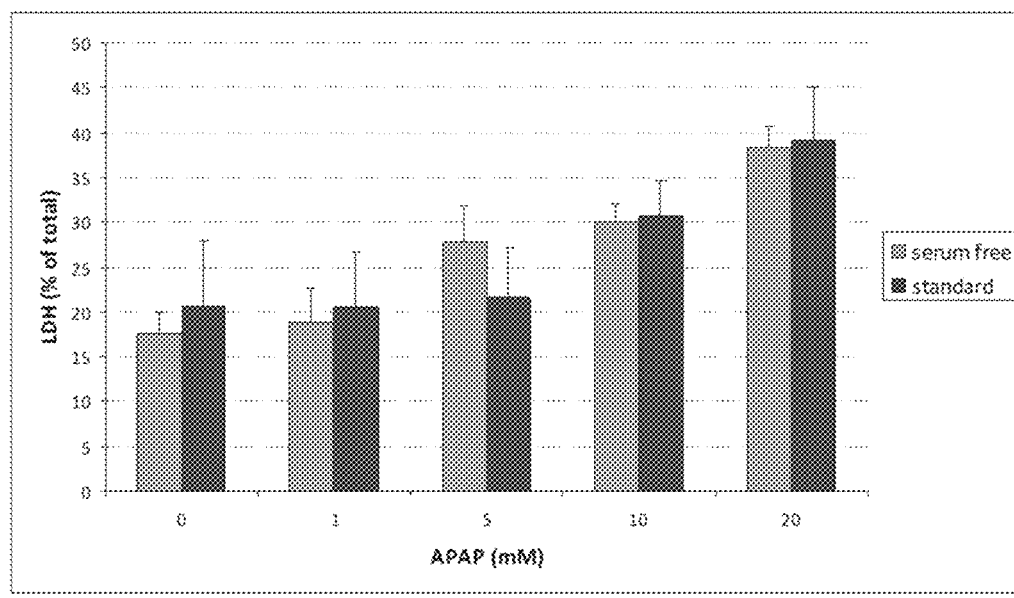
Figure 2C:
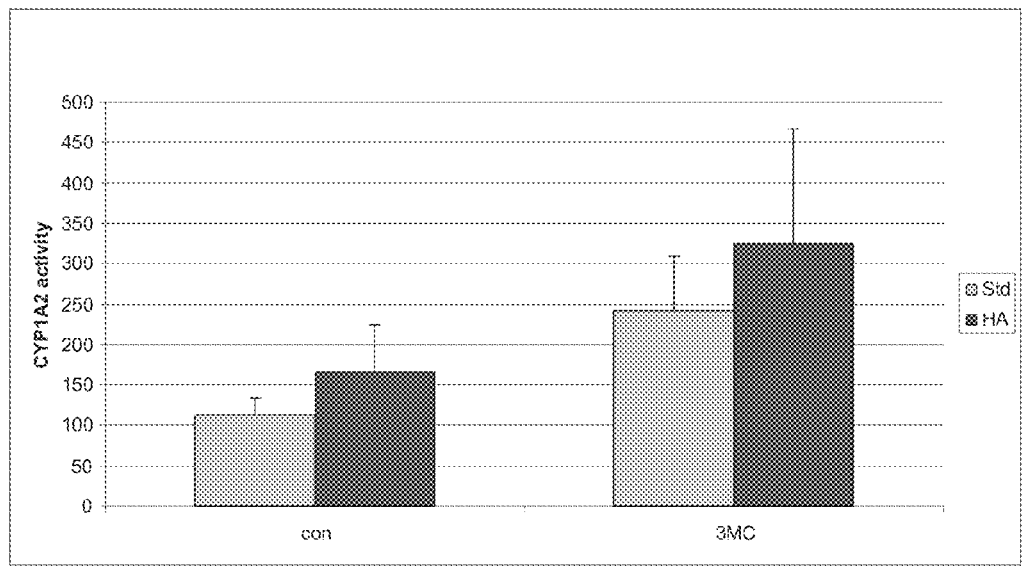
Figure 2D:
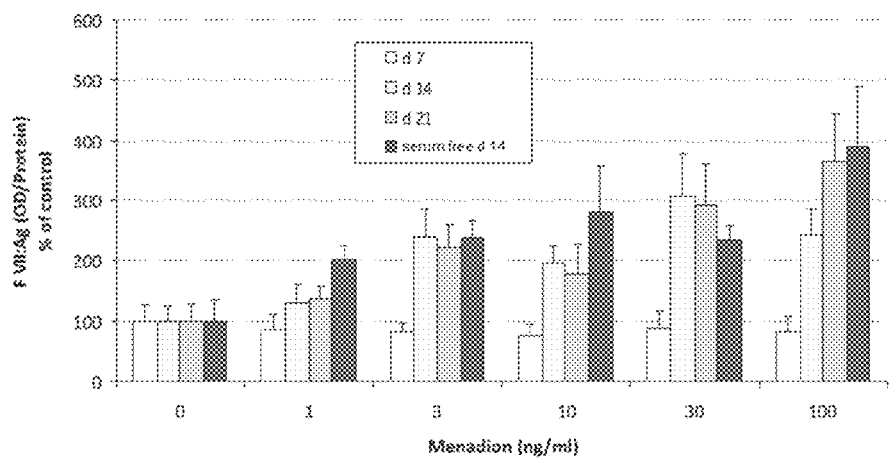
Figure 2E:
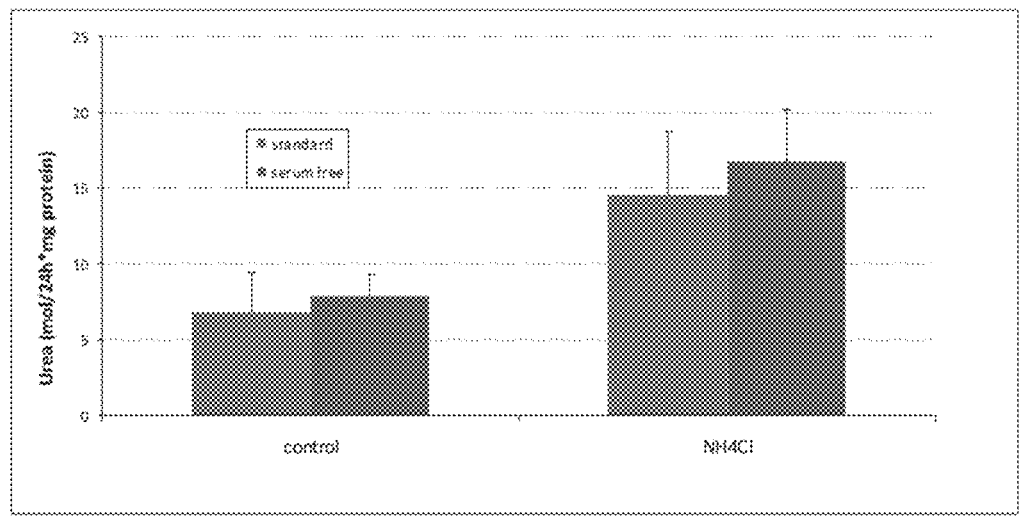
Figure 2F:
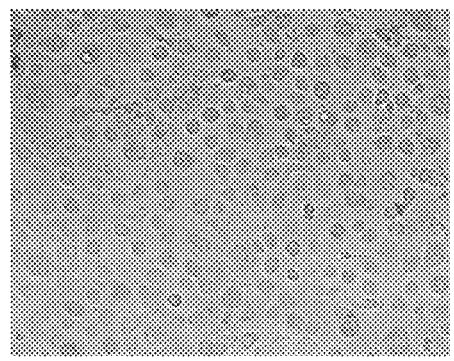
Figure 2F:
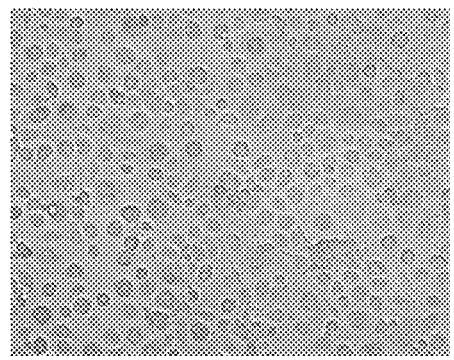
Figure 3A:
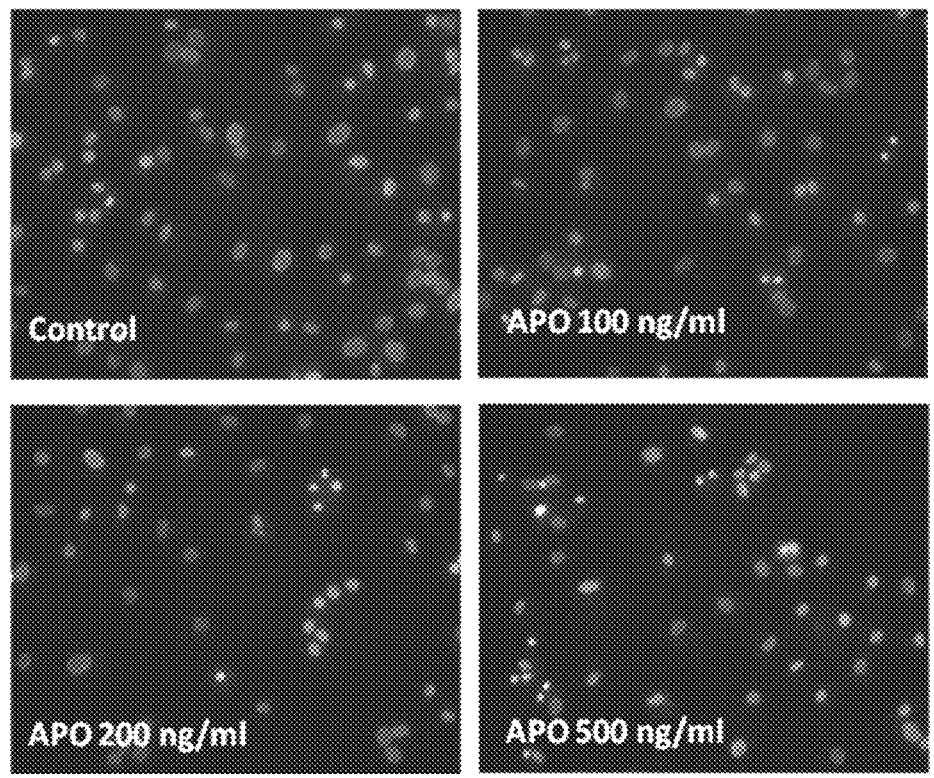
FIG. 3: Induction of apoptosis in the cells of the present invention
- (a) Induction of apoptosis as measured by nuclear condensation visualized by HOECHST 33342 as marker of apoptosis in the cells of the present invention cultured for 21 days after incubation with different concentrations of the CD95 binding antibody APO for 24 hours
- (b) Caspase-3 activity in the cells of the present invention cultured for different periods and treated for 24 hours with different concentrations of the CD95 binding antibody APO.
Figure 3B:
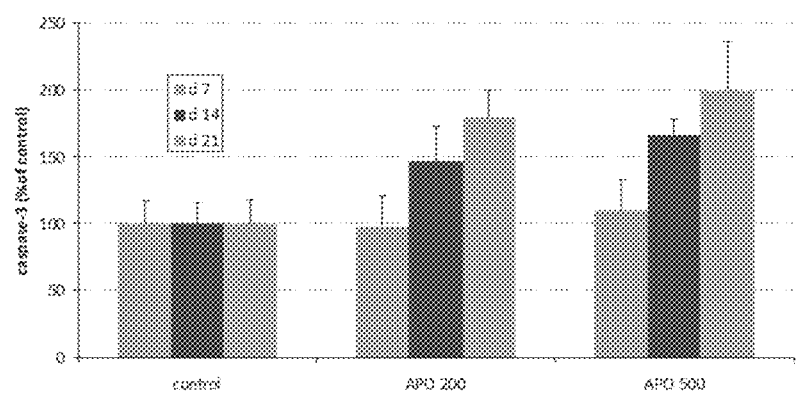
Figure 4A:
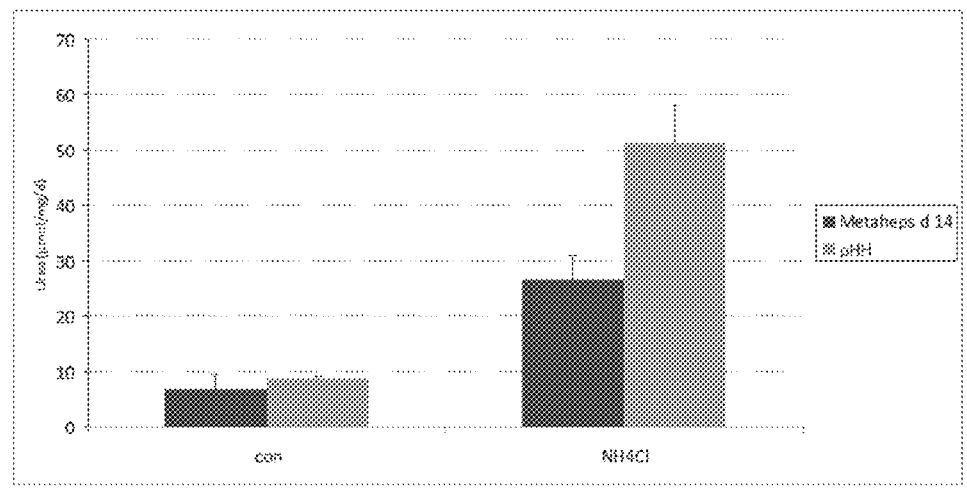
FIG. 4: Comparison of hepatocyte-specific characteristics between the cells of the present invention (Metaheps) and primary human hepatocytes (pHH)
- (a) Urea synthesis normalized on cell protein (determined photometrically using the QuantiChrome™ Urea Assay Kit) under basal conditions and after treatment with 100 µM NH$_4$Cl in primary human hepatocytes (culture day 4) and cells of the present invention (day 14) derived from the same donor
- (b) Induction of cytochrome CYP3A activity by treatment with 50 rifampicin for 24 hours in primary human hepatocytes (culture day 6) and cells of the present invention cultured for 14 days wherein the primary human hepatocytes and the cells of the present invention are derived from the same donor
- (c) Specific enzyme activities of DPP-IV, γ-GT (GGT) and ALT in primary human hepatocytes (culture day 4) and cells of the present invention cultured for 14 days, wherein the primary human hepatocytes and the cells of the present invention are derived from the same donor
Figure 4B:
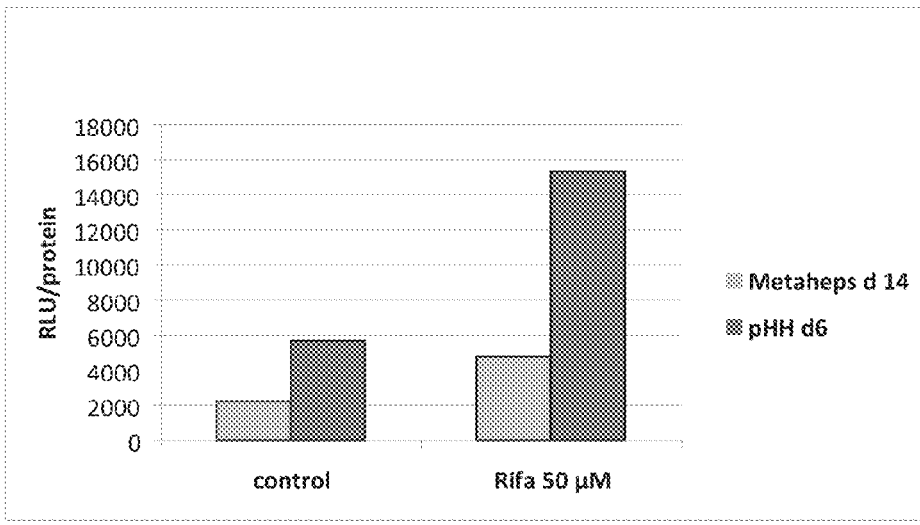
Figure 4C:
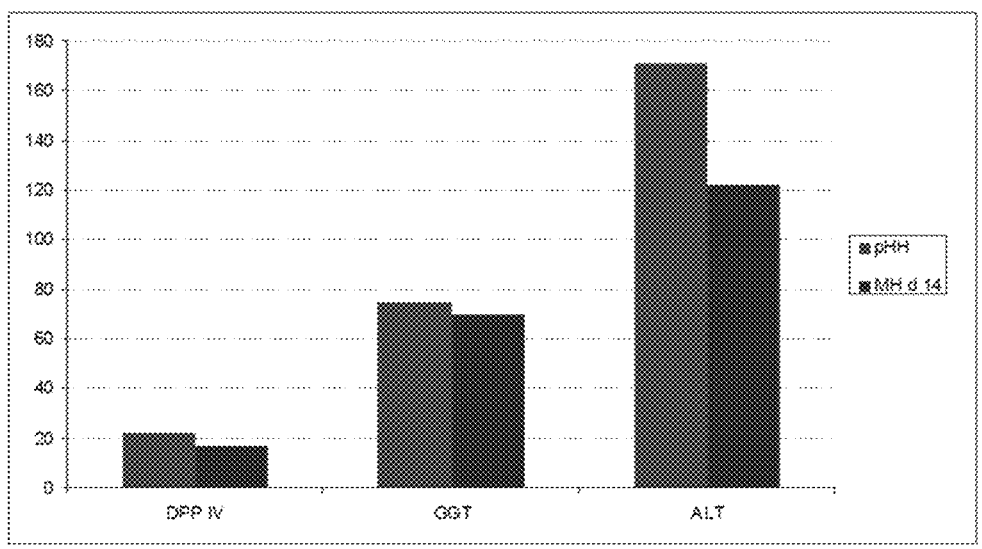
Figure 5A:
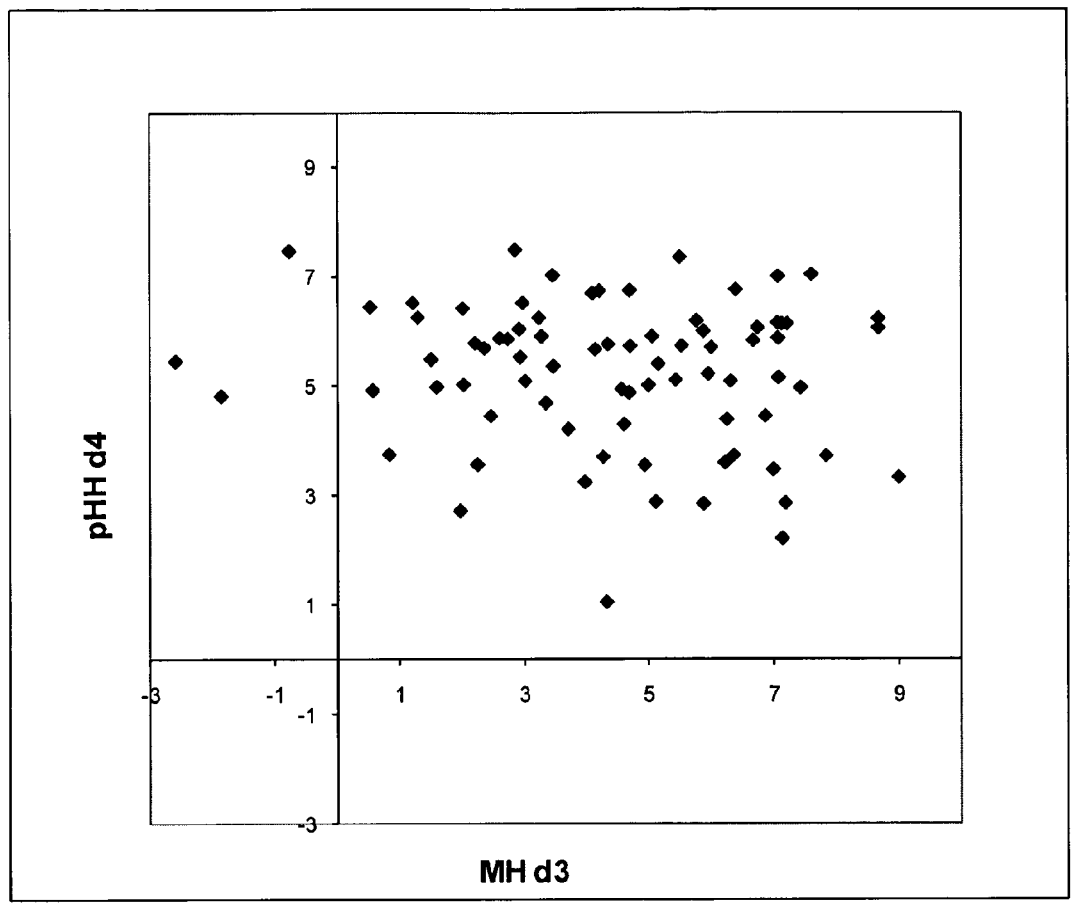
FIG. 5: Comparison of the gene expression pattern between the cells of the present invention (Metaheps, MH) and primary human hepatocytes
- a) Correlation of gene expression patterns in Metaheps on culture days 3, 7 and 14 and primary human hepatocytes (culture day 4) of the same donor
  X- and Y-axis are log$_2$ gene-expression normalized on beta-actin.
- b) Adaption of gene-expression in Metaheps to primary hepatocyte gene expression (on day 4 of culture) on culture days 3 (upper panel), day 7 (middle panel) and day 14 (lower panel). The darkest part shows the percentage of genes with very good adaptation, while the lightest part shows the percentage of genes which were not detectable.
- c) Comparison of gene groups coding for genes with specific physiological functions in Metaheps (culture day 14) and primary human hepatoctyes (culture day 4)
Figure 5A:
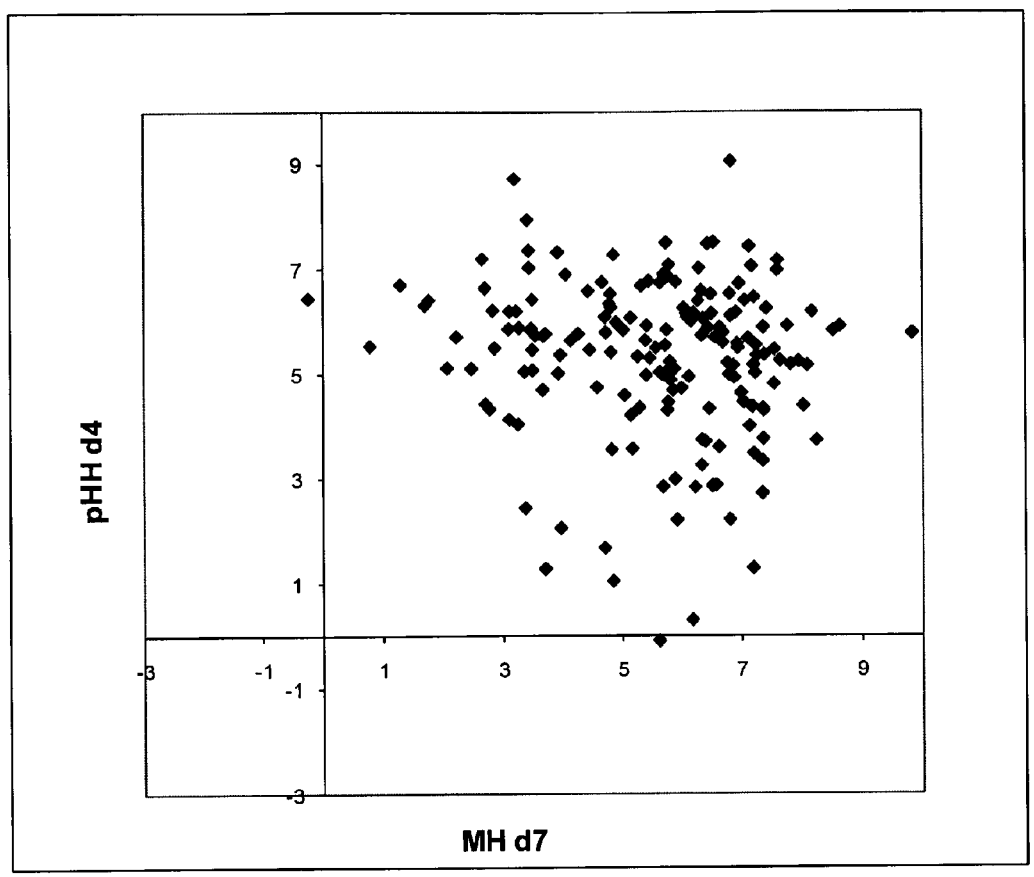
Figure 5B:
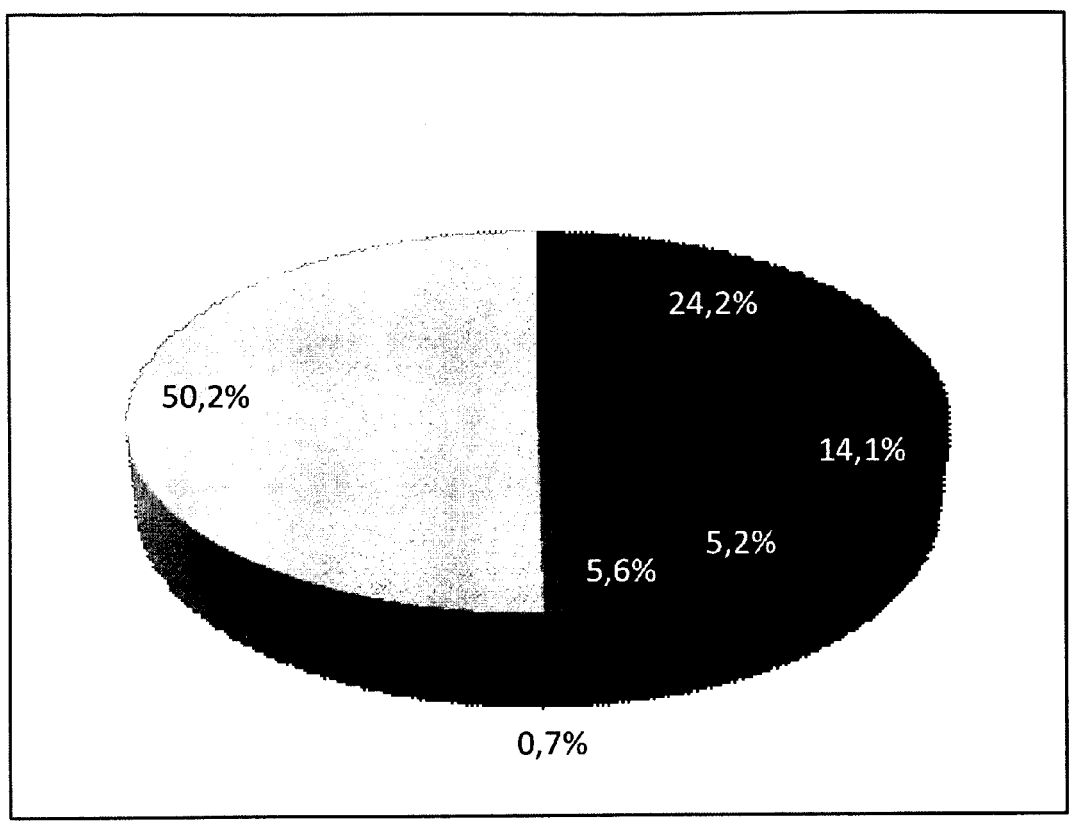
Figure 5C:
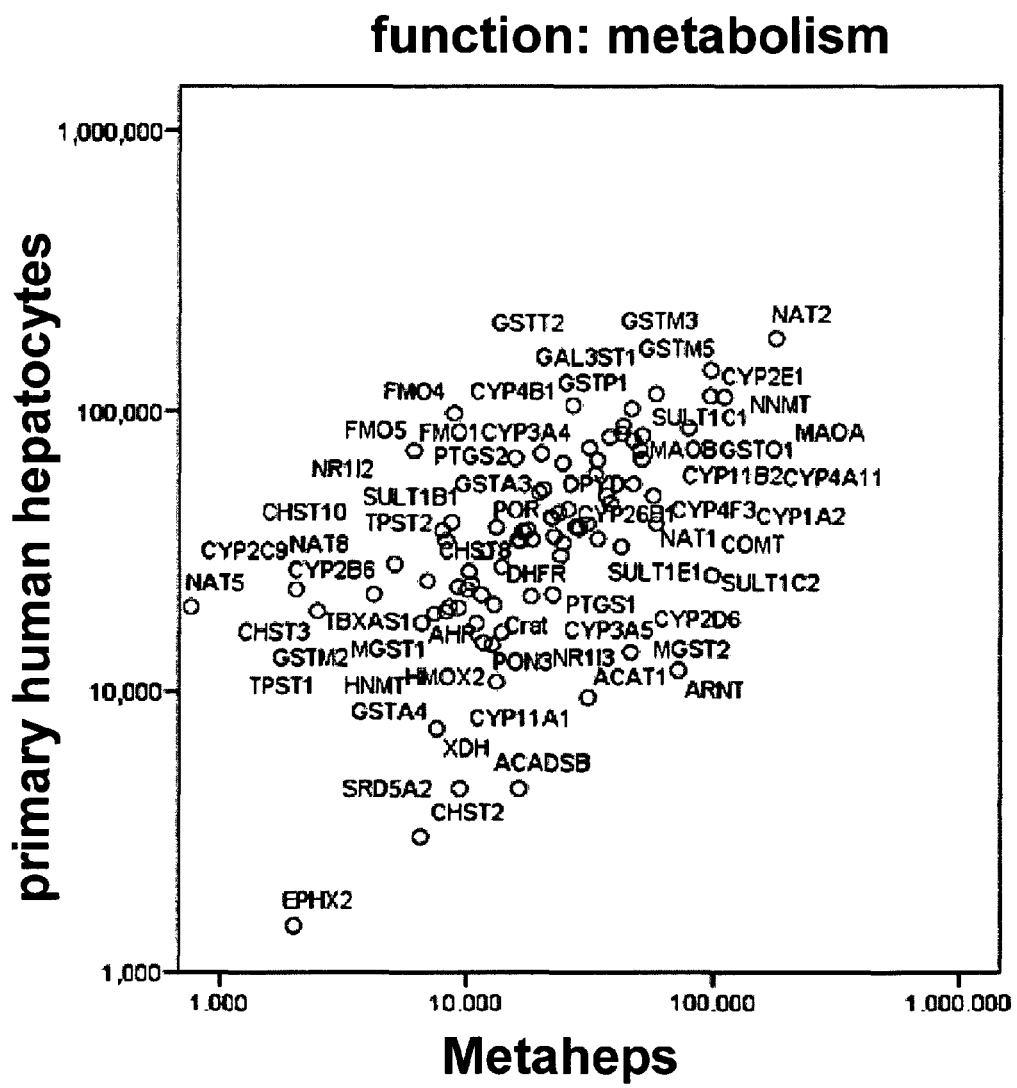
Figure 6A:
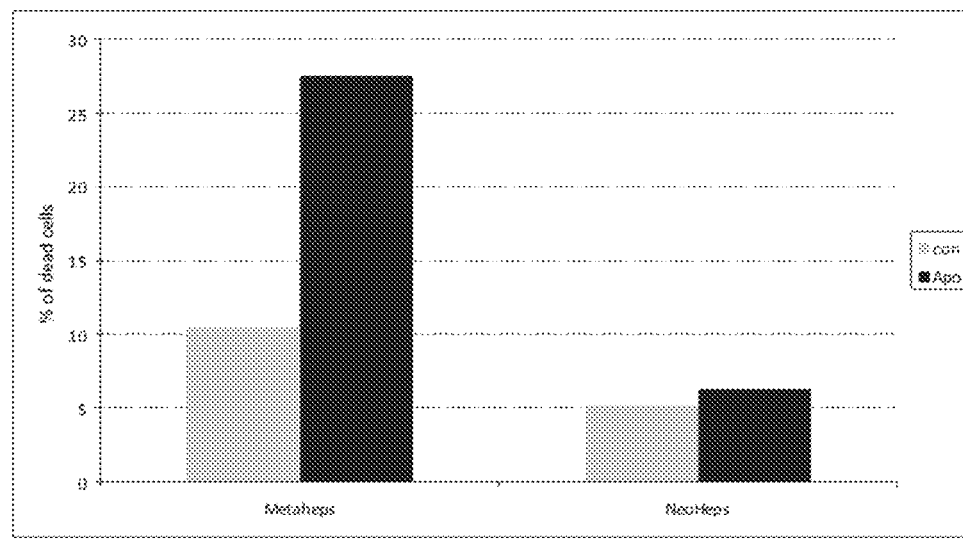
FIG. 6: Comparison of the cells of the present invention (culture day 14) with primary human hepatocytes (culture day 4) and/or neo-heaptocytes (neoheps) (culture day 14) established by the method described in Ruhnke et al. (2005) Gastroenterology 128(7): 1774-1786
   (a) Induction of apoptosis as measured by staining the cells with propidium iodide and subsequent FACS analysis in cells of the present invention (Metaheps) and NeoHeps derived from the same donor 500 ng/ml APO for 24 hours
   (b) Factor VIII synthesis in cells of the present invention (Metaheps), primary hepatocytes and NeoHeps (normalized to protein, presented as % of primary hepatocytes)
   (c) Factor VII synthesis in cells of the present invention (Metaheps), primary hepatocytes and NeoHeps (normalized to protein, presented as % of primary hepatocytes)
   (d) Inhibition of CYP1A2 activity in cells of the present invention (MH) cultured under standard (i.e. 10% FCS) and serum-free conditions and in NeoHeps (NH) by treatment of the cells with 500 µM caffeine as determined by the fluorescent substrate 3CEC
Figure 6B:
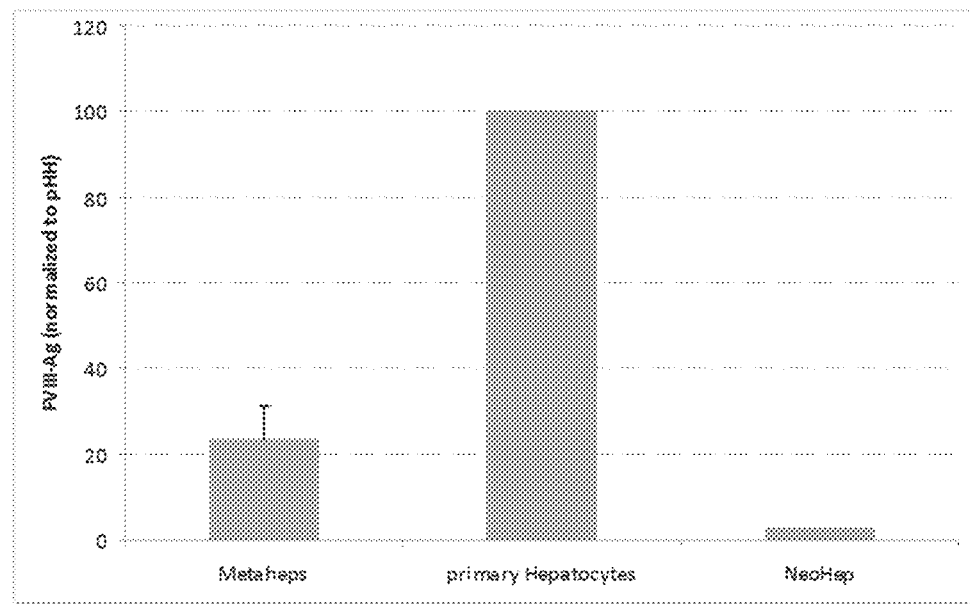
Figure 6C:
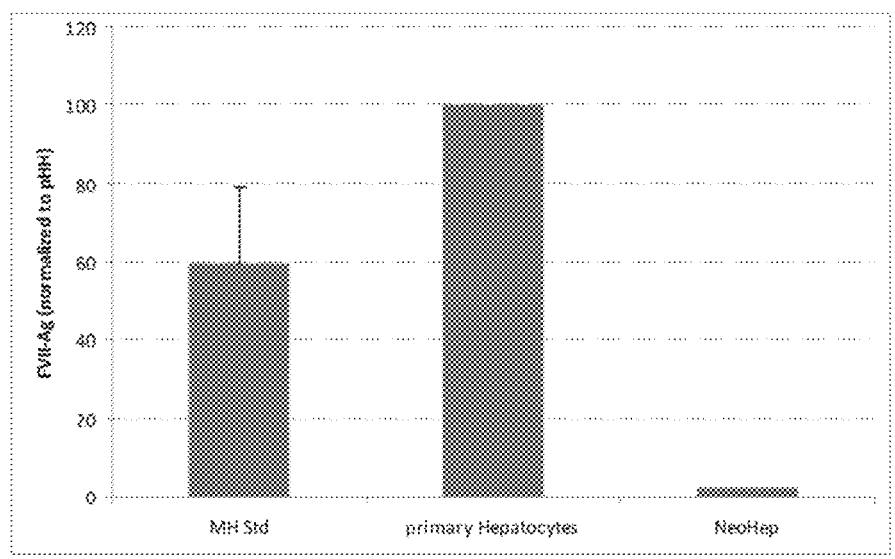
Figure 6D:
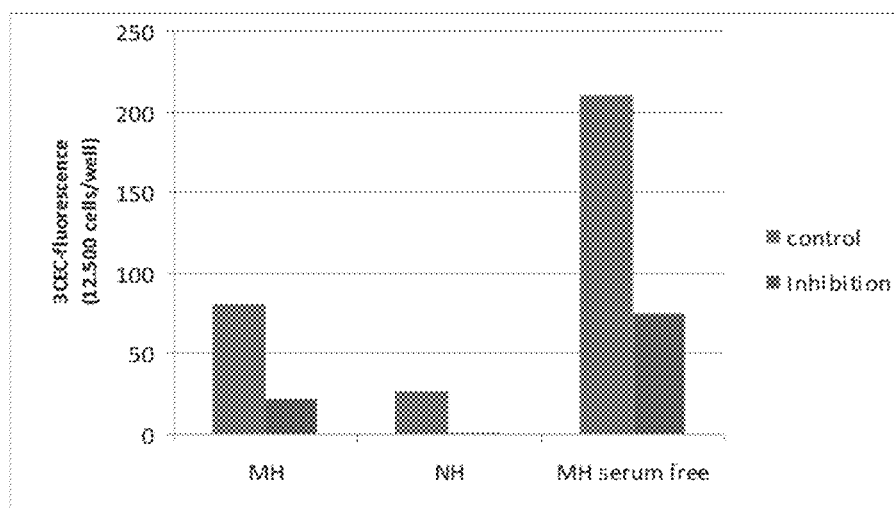
Figure 7:
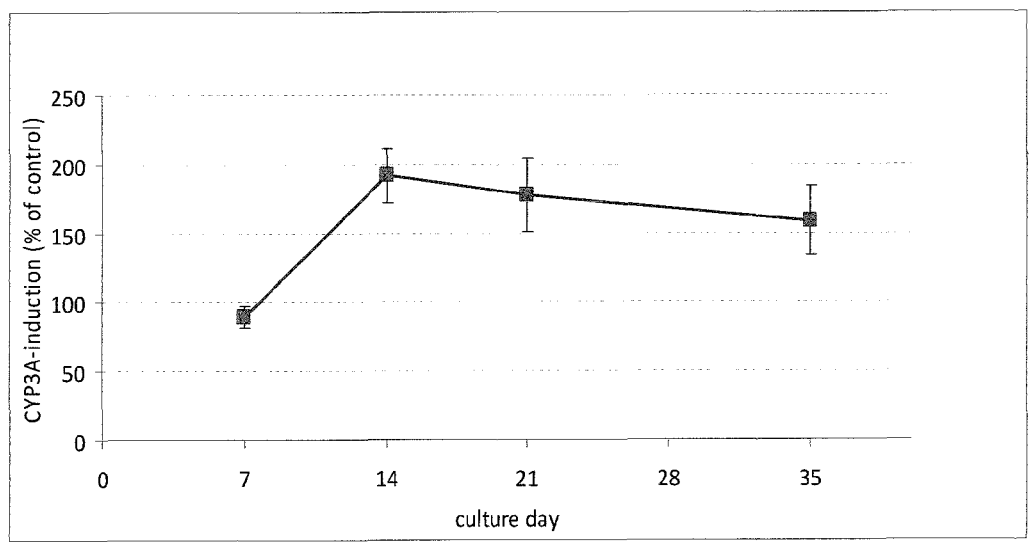
FIG. 7: Long term stability of CYP3A activities inducible by treatment with 10 µM phenyloin for 48 h in cells of the present invention from culture day 14 to 35 determined by using the luminescent P450 Glo assay (Promega).
Figure 8A:
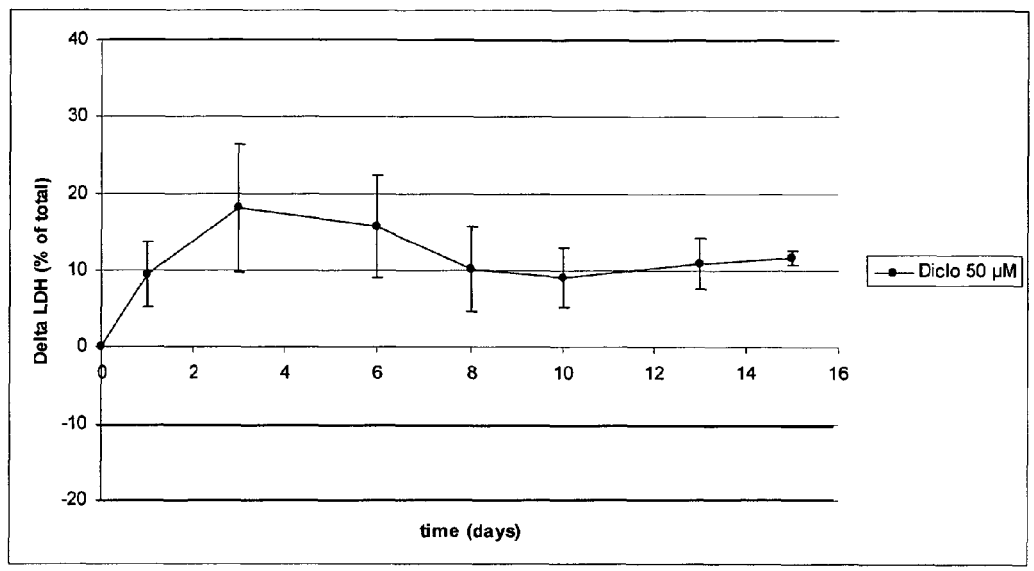
FIG. 8: Long term toxicity in cells of the present invention cultured for 15 days in low concentrations of (a) diclofenac (50 µM) and (b) acetaminophen (500 µM) as measured by LDH activity
Figure 8B:
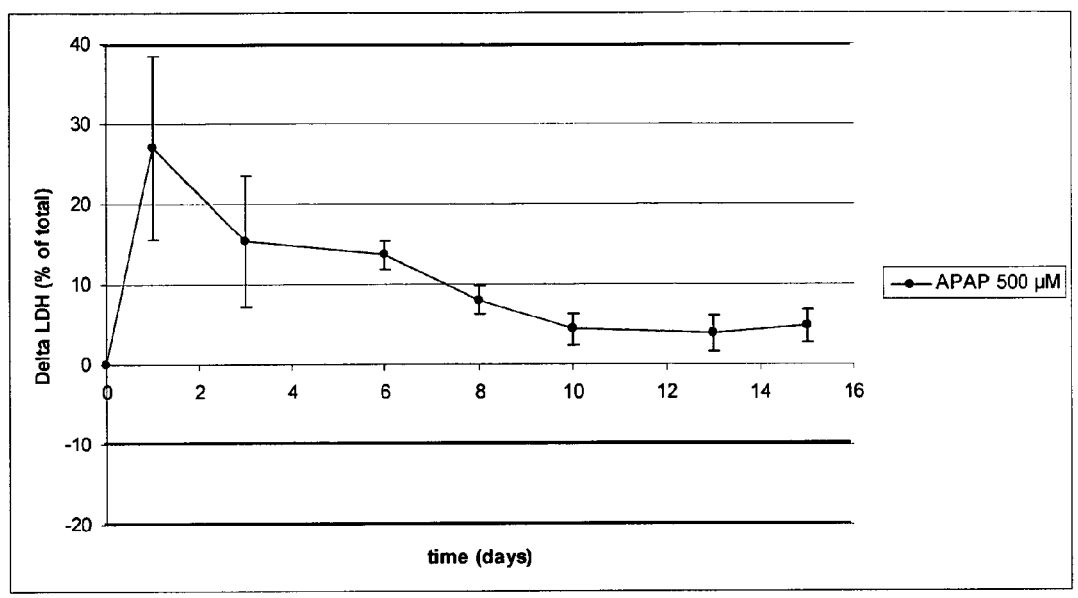
Figure 9:
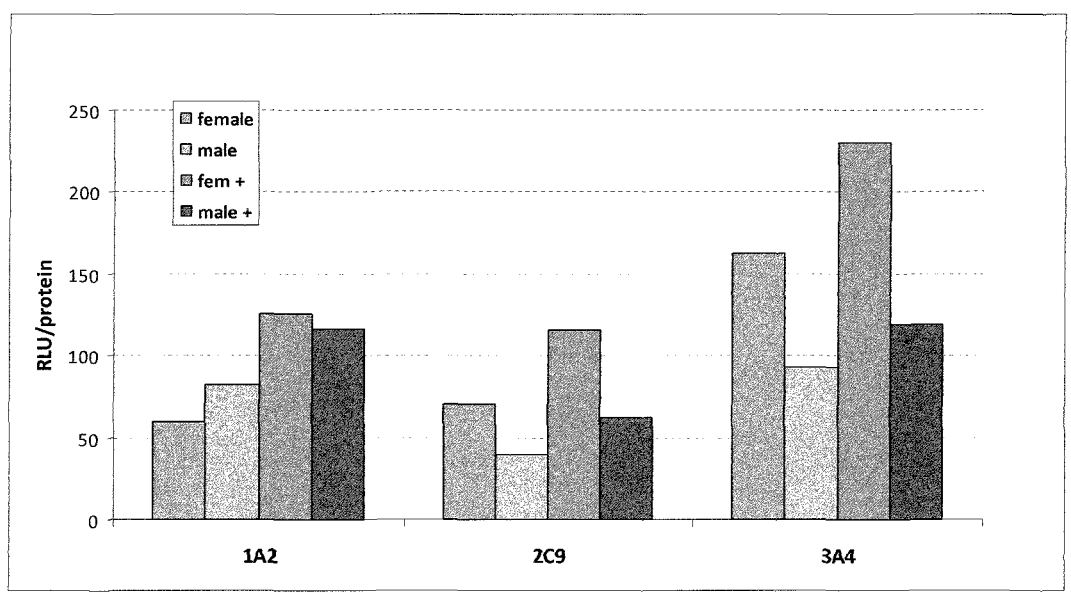
FIG. 9: Gender differences in activities of CYP1A2, 2C9 and 3A4 in cells of the present invention isolated from either male or female humans on culture day 14 determined by the luminescent method; "+" behind male or female means the activity after induction with 1 µM 3-methylcholanthrene for CYP1A2 and 50 µM rifampicin for CYP3A4 and CYP2C9

Before describing in detail exemplary embodiments of the present invention, the following general definitions are provided.

The present invention as illustratively described in the following may suitably be practiced in the absence of any element or elements, limitation or limitations, not specifically disclosed herein.

The present invention will be described with respect to particular embodiments but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. a cell is defined to be obtainable by a specific method, this is also to be understood to disclose a cell which is obtained by this method.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

The term "human hepatocytes" means cells of the main tissue of the human liver which are involved in protein synthesis and storage, transformation of carbohydrates, synthesis of cholesterol, bile salts and phospholipids as well as detoxification of exogenous and endogenous substances. Primary human hepatocytes in culture usually display a hexagonal morphology and establish confluent cell layers including intercellular contacts made by gap junctions and an epithelial phenotype as determined by the expression of epithelial marker proteins such as cytokeratin 18 and pan-actin. Primary human hepatocytes, i.e. cells isolated from liver tissue without any transformation step, can be kept in culture only for a very limited time, i.e. 8 to 14 days, without losing their properties and viability.

Typical characteristics of human hepatocytes include, but are not limited to:
   activity of enzymes such as:
      dipeptidyl peptidase IV (DPP-IV) as measured, e.g., with the chromogenic substrate Gly-Pro-p-nitroanilide (Bauvois (1990) Eur. J. Immunol 20(3): 459-68);
      alanine aminotransferase (ALT) as measured, e.g., with the ALT-Kit purchased from Randox-Laboratories according to the manufacturer's instructions;
      gamma glutamyl transpeptidase (γ-GT), e.g. by determining the amount of p-nitroaniline resulting from the γ-GT catalyzed reaction of L-gamma-glutamyl-p-nitroanilide and glycylglycine to gamma-glutamyl-glycylglycide and p-nitroaniline may be determined (Szasz G: Gamma-glutamyl-transpeptidase, in: Methoden der Enzymatischen Analyse, 3rd ed., (Vol 1), edited by Bergmeyer H U, Weinheim/Bergstr., Verlag Chemie, 1974, pp 757-762);
      lactate dehydrogenase (LDH) as measured, e.g., using the cytotoxicity Kit obtained from Promega according to the manufacturer's instructions;
   secretion of glucose after glucagon stimulation as measured by photometric determination of NADPH using the Hexokinase/Glucose-6-phosphate Dehydrogenase-method (Bondar et al. (1974) Clin Chem 20/5: 586-590)
   ability to metabolize pharmacological substances such as acetaminophen (APAP) and diclofenac as measured for example by the release of the cytoplasmic enzyme LDH into the medium upon treatment with a selected pharmacological substance;
   expression of albumin, α-fetoprotein, asialoglycoprotein receptors 1 and 2, carbamoyl phosphate synthetase (1) and coagulation factors I and II as measured for example by Western Blot or RT-PCR analysis;
   expression of CYP 450 enzymes such as CYP1A2, CYP2A6, CYP2D6, CYP2P8-9, CYP2E1, CYP3A3-5, CYP2C9, CYP3A4 as measured for example by Western Blot or RT-PCR analysis;
   activity of CYP 450 enzymes such as CYP1A2, CYP2C9 and CYP3A4 as measured by luminescence (e.g. using P450-Glo-Assays (Promega) according to the manufacturer's instructions) or fluorescence (3-cyano-coumarine; Donato et al. (2004) Drug Metabolism and Disposition 32(7): 699-706);
   ability to synthesize urea after incubation with ammonium ions as measured for example by an enzymatic urea test (e.g. QuantiChrome™ Urea Assay Kit of Clonagen (Brussels, Belgium) according to the manufacturer's instructions);

ability to produce factor VII after incubation with vitamin K as measured for example by direct ELISA for factor VII in the cell culture medium;

ability to produce factor VIII as measured for example by sandwich-ELISA for factor VIII in the cell culture medium (Esposito et al. (2000) Kidney Int. 58:123-130; Ziyadeh et al. (1990) Am. J. Physiol. 259: F704-F714);

secretion of albumin as measured for example by ELISA of the cell culture medium;

expression of xenobiotic transporters such as proteins of the ABC-transporter family as measured for example by export of the fluorescent dyes rhodamine-123 or HOECHST 33342 (Brown C D (2008) Toxicol. Appl. Pharmacol. 233(3): 428-38); and gene expression patterns, e.g. of different CYP P450 genes and transcription factors such as E2F and of the RAR, RXR and PPAR families.

Details of suitable test methods for determining the above characteristics are described in the examples section below.

The cells produced by the method of the present invention show at least one, preferably two or three, more preferably four or five, even more preferably six, seven or eight and most preferably all of the above-listed characteristics.

In the process of the present invention, the above characteristics are preferably measured after the cells have been cultured for at least four days and not more than 42 days in the cell culture medium comprising FGF-4. More preferably, the characteristics are measured after the cells have been cultured for seven to 14 days in the cell culture medium comprising FGF-4 and most preferably the characteristics are measured after the cells have been cultured for 14 days in the cell culture medium comprising FGF-4.

The term "monocyte" refers to the leukocyte type which is characterized by high level expression of the cell surface antigen CD14.

These monocytes are usually obtained from whole blood treated with an anti-coagulant such as heparin, EDTA or citrate. The whole blood may be stored for up to 24 hours at 4° C. before the monocytes are isolated.

The whole blood can be separated into plasma and white and red blood cells preferably by density gradient centrifugation, wherein after the centrifugation the plasma is found in the supernatant below which there is a layer which contains the totality of the white blood cells, which layer is also referred to "buffy coat". Below this "buffy coat" there is a phase containing the red blood cells. The "buffy coat" layer is then isolated and separated to obtain the monocytes, e.g. by centrifugation using a known process. For example, the "buffy coat" layer may be coated onto a lymphocyte separation medium such as Ficoll Hypaque and centrifuged. If the "buffy coat" is contaminated with erythrocytes, as apparent by the red staining of the "buffy coat", the cells are incubated with an erythrocyte lysis buffer containing $NH_4Cl$, $KHCO_3$ and EDTA.

Alternatively, the monocytes can be obtained from whole blood by methods such as FACS, immunomagnetic bead sorting and magnetic-activated cell sorting on the basis of their expression of cell surface markers such as CD14.

The monocytes to be used in the method of the present invention can be obtained from any isolated human blood and the blood can also originate from organs such as the spleen, lymph nodes or bone marrow. In another embodiment of the present invention, the monocytes are isolated from ascites.

If the cells of the present invention, i.e. the cells having at least one characteristic of human hepatocytes, are intended to be used in cell therapy, the monocytes used as starting material in the method of the present invention are preferably autologous monocytes, i.e. monocytes originating from the blood of the patient who is subsequently to be treated with the cells of the present invention.

The term "seeding the cells" generally refers to introducing a cell mixture into an in vitro environment capable of promoting the survival and/or growth of the introduced cells or at least a certain population within the cell mixture such as the cells having at least one characteristic of human hepatocytes in the present case. The cells seeded in the method of the present invention are monocytes obtained from a suitable source such as peripheral blood or ascites. In a preferred embodiment the cells are seeded immediately after their isolation. However, it is also possible to introduce one or more additional steps between the isolation and the seeding, such as freezing or centrifuging the cells.

The cells are seeded at a density of 100,000-400,000 cells/$cm^2$ of the culture vessel, preferably at a density of 150,000-350,000 cells/$cm^2$ of the culture vessel, more preferably at a density of 200,000-300,000 cells/$cm^2$ of the culture vessel and most preferably at a density of 250,000 cells/$cm^2$ of the culture vessel.

The cells may be seeded in a cell culture medium comprising IL-3 and adenosine and optionally M-CSF. However, the cell culture medium into which the cells are seeded may also lack IL-3, adenosine and M-CSF, if the medium is to be changed within one hour, preferably within 20 minutes, after seeding the cells.

A "culture vessel" is any vessel which is suitable for growing cells in a culture medium or agar, either in fluid phase or adhered to an interior surface of the vessel. Types of such specialized vessels include roller bottles, spinner flasks, petri dishes and tissue flasks. Culture vessels are designed to be incubated in temperature, humidity and gas controlled environments to facilitate maximum cell or tissue growth. Generally, a layer of cell culture medium or agar covers the growing surface.

The portion of the vessel not utilized as a growing surface encloses the interior gaseous environment which surrounds the cell culture. Cells, tissues, microorganisms and the like are typically introduced into the interior of cell culture vessels through an opening in the vessel. After introduction of the cells the opening may be closed such that the cells are not in contact with the environment during the culturing of the cells.

In a preferred embodiment of the present invention, the culture vessel is treated for tissue culture, which means that the surface of the culture vessel is treated such that cells which usually grow in an adherent state, such as human hepatocytes, grow adherently, but cells which grow in suspension do not adhere or adhere only loosely. Such treatment for tissue culture may involve the irradiation of the vessel or the coating of the vessel, for example with a special plastic, polymer or nanostructure or with proteins of the extracellular matrix. Culture vessels treated for tissue culture can comprise tissue culture dishes and tissue culture flasks and are available from different suppliers such as Becton Dickinson, Greiner, Sigma and TPP.

The terms "cell culture" and "culturing of cells" refer to the maintenance and propagation of cells, preferably human cells, in vitro. Ideally the cultured cells do not differentiate spontaneously, but only when treated with a suitable stimulus such as FGF-4 used in the method of the present invention. Unless specified otherwise, when the present disclosure provides a time period for culturing the cells of the present invention this time period comprises both step (a) and step (b) of the method of the present invention.

"Cell culture medium" is used for the maintenance of cells in culture in vitro. For some cell types, the medium may also be sufficient to support the proliferation of the cells in culture. A medium according to the present invention provides nutrients such as energy sources, amino acids and anorganic ions. Additionally, it may contain a dye like phenol red, sodium pyruvate, several vitamins, free fatty acids, antibiotics, antioxidants and trace elements.

For culturing the cells of the present invention any standard medium such as Iscove's Modified Dulbecco's Media (IMDM), alpha-MEM, Dulbecco's Modified Eagle Media (DMEM), RPMI Media and McCoy's Medium is suitable. These media are well-known to a person skilled in the art and may be purchased from companies such as Cambrex (East Rutherford, USA), Invitrogen (San Diego, USA) and Sigma-Aldrich (Deisenhofen, Germany). Preferably, the medium is DMEM/Ham's F12 (1:1).

Preferably, the medium does not contain a sulfur compound such as 2-mercaptoethanol or dimethylsulfoxide (DMSO).

However, the medium to be used in the process of the present invention may contain other conventional cell culture medium supplements such as L-glutamine, penicillin and streptomycin.

In the method of the present invention, the monocytes are first cultured in a medium containing Interleukin 3 (IL-3) and adenosine (corresponding to step (b) of the method of the present invention).

IL-3 is a cytokine which stimulates the differentiation of multipotent hematopoietic stem cells into myeloid progenitor cells and which stimulates the proliferation of all cells in the myeloid lineage including monocytes. Preferably, human IL-3 is used and most preferably recombinant human IL-3 is used. Wild-type human IL-3 may be obtained for example from R&D Systems (Minneapolis, USA), GenWay (San Diego, USA) or Miltenyi Biotech (Bergisch Gladbach, Germany).

The term "IL-3" is intended also to comprise IL-3 analogs, i.e. variants having one or more amino acid substitutions, deletions and/or additions within the amino acid sequence of the IL-3 polypeptide which variants substantially maintain the receptor binding properties and the biological activity such as stimulating the proliferation of myeloid cells of wild-type IL-3. Suitable IL-3 analogs are described for example in Lopez et al. (1992) Proc. Natl. Acad. Sci. USA 89:11842-11846 and include IL-3 having an alanine on position 101, IL-3 having valine on position 116 and an IL-3 having alanine on position 101 and valine on position 116 of the polypeptide.

The IL-3 is present in the cell culture medium in step (b) and, optionally, step (c) of the method of the present invention in a concentration of 0.2 ng/ml to 2.5 ng/ml or 0.3 ng/ml to 2 ng/ml, preferably 0.4 ng/ml to 1.8 ng/ml or 0.5 ng/ml to 1.7 ng/ml, more preferably of 0.6 ng/ml to 1.6 ng/ml or 0.7 ng/ml to 1.5 ng/ml, even more preferably 0.8 ng/ml to 1.4 ng/ml or 0.9 ng/ml to 1.1 ng/ml and most preferably 1 ng/ml.

Adenosine is a nucleoside composed of a molecule of adenine attached to ribose sugar molecule moieties. It plays an important role in biochemical processes such as energy transfer and signal transduction. The term "adenosine" is intended also to comprise analogs of adenosine which bind to adenosine A3 receptor and potentiate the stimulatory effect of IL-3, such as $N^6$-(3-iodobenzyl)adenosine-5'-N-methyluronamide (IB-MECA) (Hofer et al. (2009) Physiol. Res. 58: 247-252). The adenosine may be obtained from suitable suppliers such as Sigma-Aldrich, Deisenhofen, Germany.

The adenosine is present in the cell culture medium in step (b) and, optionally, step (c) of the method of the present invention in a concentration of 10-300 nM or 20-280 nM, preferably 30-250 nM or 40-220 nM, more preferably 50-200 nM or 60-180 nM, even more preferably 80-150 nM or 90-120 nM and most preferably 100 nM.

In a preferred embodiment of the present invention the cell culture medium comprises 0.2-2.5 ng/ml IL-3 and 10-300 nM adenosine, more preferably 0.6-1.6 ng/ml IL-3 and 50-200 nM adenosine, even more preferably 0.8-1.4 ng/ml IL-3 and 80-150 nM adenosine and most preferably 1 ng/ml IL-3 and 100 nM adenosine.

In a preferred embodiment, the medium used in step (b) and, optionally, step (c) of the method of the present invention further comprises macrophage colony-stimulating factor (M-CSF).

M-CSF (also referred to as CSF-1) is a cytokine produced by monocytes, fibroblasts and endothelial cells which induces the division of monocytes upon binding to its specific c-Fms receptor (also referred to as CSF-1R). Preferably, human M-CSF is used and most preferably recombinant human M-CSF is used. The M-CSF used in the cell culture medium may be obtained from suitable suppliers such as R&D Systems (Minneapolis, USA) or Sigma Aldrich (Deisenhofen, Germany).

The term "M-CSF" within the meaning of the present invention is intended also to comprise an analog of M-CSF which comprises one or more amino acid substitutions, deletions and/or additions with respect to the wild-type M-CSF amino acid sequence and which retains receptor binding and biological activity of M-CSF. Suitable M-CSF analogs include (Q17A, R21A) M-CSF and (E115A, N119A) M-CSF which are described for example in Taylor et al. (1994) J. Biol. Chem. 269(49): 31171-31177.

The M-CSF is present in the cell culture medium in step (b) and, optionally, step (c) of the method of the present invention in a concentration of 0.1 ng/ml to 7 ng/ml or 0.2 to 5 ng/ml, preferably 0.25 ng/ml to 3 ng/ml or 0.3 ng/ml to 2.5 ng/ml, more preferably 0.35 ng/ml to 1.0 ng/ml or 0.4 ng/ml to 0.8 ng/ml and most preferably 0.5 ng/ml.

In a preferred embodiment of the present invention the cell culture medium in step (b) comprises 0.2-2.5 ng/ml IL-3, 10-300 nM adenosine and 0.1 ng/ml-7 ng/ml M-CSF, more preferably 0.6-1.6 ng/ml IL-3, 50-200 nM adenosine and 0.3 ng/ml-2.5 ng/ml M-CSF, even more preferably 0.8-1.4 ng/ml IL-3, 80-150 nM adenosine and 0.4 ng/ml-0.8 ng/ml M-CSF and most preferably 1 ng/ml IL-3, 100 nM adenosine and 0.5 ng/ml M-CSF.

The cells are cultured in the cell culture medium comprising IL-3 and adenosine and optionally M-CSF, but not FGF-4, for at least 4 days, preferably at least 5 days, more preferably at least 6 days and most preferably for 7 days. The cells are cultured in the cell culture medium comprising IL-3 and adenosine and optionally M-CSF, but not FGF-4, for no more than ten days, preferably no more than nine days, more preferably no more than eight days and most preferably for seven days. Preferably, the cells are cultured in the cell culture medium comprising IL-3 and adenosine and optionally M-CSF, but not FGF-4, for at least 4 days and no more than ten days.

In a second culturing step of the method of the present invention (corresponding to step (c) of the method of the present invention) the cells are cultured in a cell culture medium comprising fibroblast growth factor 4 (FGF-4). In a preferred embodiment, the cell culture medium used in the first culturing step is removed and the cell culture medium comprising FGF-4 is added, i.e. the cells are cultured in the cell culture medium comprising FGF-4 subsequent to the culturing of the cells in the cell culture medium comprising IL-3 and adenosine and (optionally) M-CSF. The cell culture medium used in the second culturing step may be the same as or different from the cell culture medium used in the first culturing step. Hence, the medium may comprise IL-3, adenosine, (optionally) M-CSF and FGF-4 together or it may only comprise FGF-4. Preferably, the cell culture medium used in the second culturing step of the present invention does not comprise IL-3, M-CSF and adenosine. However, residual amounts, i.e. no more than 50% or 40%, preferably no more than 30% or 20%, more preferably no more than 15% or 10% and most preferably no more than 5% or 2% of the concentration in the first culturing step, of IL-3, adenosine and (optionally) M-CSF may be present in the second culturing step. In a further embodiment, the cells may be incubated in a medium comprising IL-3, adenosine, (optionally) M-CSF and FGF-4 immediately after seeding the cells, Further, the basic medium used in the second culturing step may be the same as or different from the basic medium used in the first step, e.g if DMEM/Ham's F 12(1:1) is used in the first step, the medium used in the second step may also be DMEM/Ham's F12 (1:1) or it may be for example RPMI. Preferably, the medium used in the first and the second culturing step is the same and most preferably, the medium used in the first and the second culturing step is DMEM/Ham's F12 (1:1).

Fibroblast growth factors are a family of growth factors involved in angiogenesis, wound healing and embryonic development. They are heparin-binding proteins and interactions with cell surface associated heparan sulfate proteoglycans have been shown to be essential for FGF signal transduction. Preferably, human FGF-4 and most preferably recombinant human FGF-4 is used. Recombinant human FGF-4 may be obtained from suitable suppliers such as R&D Systems (Minneapolis, USA).

The concentration of FGF-4 in the cell culture medium in step (c) of the method of the present invention is 0.5-7 ng/ml, preferably 1-5 ng/ml, more preferably 2-4 ng/ml and most preferably 3 ng/ml.

In a preferred embodiment of the present invention, the cell culture medium used in the second culturing step of the present invention further comprises at least one compound selected from the group consisting of epidermal growth factor (EGF), glucagon, insulin and heparin, more preferably, the cell culture medium used in the second culturing step of the present invention further comprises EGF, glucagon and insulin and most preferably the cell culture medium used in the second culturing step of the present invention further comprises EGF, glucagon, heparin and insulin. EGF is a growth factor that plays an important role in the regulation of cell growth, proliferation, differentiation and survival. If present, the concentration of EGF in the cell culture medium in the second culturing step is 5-20 ng/ml, preferably 7-15 ng/ml, more preferably 8-12 ng/ml and most preferably 10 ng/ml. Preferably, human EGF and more preferably recombinant human EGF is used. The EGF used in the cell culture medium may be obtained from suitable suppliers such as Biochrom AG, Berlin, Germany.

Glucagon is a hormone which is secreted by the pancreas and which causes the liver to convert stored glycogen into glucose which is then released into the bloodstream. If present, the concentration of glucagon in the cell culture medium in the second culturing step of the method of the present invention is 2-10 nM, preferably 3-8 nM, more preferably 4-7 nM and most preferably 5 nM. Preferably, human glucagon and more preferably recombinant human glucagon is used. The glucagon used in the cell culture medium may be obtained from suitable suppliers such as Sigma-Aldrich, Deisenhofen, Germany.

Insulin is a peptide hormone which is produced by the islets of Langerhans in the pancreas which regulates the energy and glucose metabolism in the body. If present, the concentration of insulin in the cell culture medium in the second culturing step of the method of the present invention is 0.10-0.50 IU, preferably 0.15-0.40 IU, more preferably 0.17-0.35 IU, even more preferably 0.20-0.30 IU and most preferably 0.28 IU. Preferably, human insulin and more preferably recombinant human insulin is used. The insulin used in the cell culture medium may be obtained from suitable suppliers such as Biochrom AG, Berlin, Deutschland.

Heparin is a highly sulfated glycosaminoglycan which is widely used as an injectable anti-coagulant. If present, the concentration of heparin in the cell culture medium in the second culturing step of the method of the present invention is 2-10 IU/ml, preferably 3-8 IU/ml, more preferably 4-7 IU/ml and most preferably 5 IU/ml. The heparin used in the cell culture medium may be obtained from suitable suppliers such as Biochrom AG, Berlin, Germany.

Preferably, the cell culture medium in the second culturing step comprises 5-20 ng/ml EGF, 2-10 nM glucagon, 0.10-0.50 IU insulin, and 2-10 IU/ml heparin. More preferably, the cell culture medium in the second culturing step comprises 8-12 ng/ml EGF, 3-8 nM glucagon, 0.17-0.35 IU insulin, and 3-8 IU/ml heparin and most preferably the cell culture medium in the second culturing step comprises 10 ng/ml EGF, 5 nM glucagon, 0.28 IU insulin and 5 IU/ml heparin.

In an even more preferred embodiment of the present invention the cell culture medium in the second culturing step comprises 0.5-7 ng/ml FGF-4, 5-20 ng/ml EGF, 2-10 nM glucagon, 0.10-0.50 IU insulin and 2-10 IU/ml heparin, and even more preferably it comprises 1-5 ng/ml FGF-4, 8-12 ng/ml EGF, 3-8 nM glucagon, 0.17-0.35 IU insulin, and 3-8 IU/ml heparin. In a most preferred embodiment of the present invention, the cell culture medium in the second culturing step comprises 3 ng/ml FGF-4, 10 ng/ml EGF, 5 nM glucagon, 0.28 IU insulin and 5 IU/ml heparin.

In a preferred embodiment, the cell culture medium used in the second culturing step of the method of the present invention does not contain hepatocyte growth factor (HGF).

The cell culture medium used in the first and second culturing step may comprise further compounds such as bile acids or bile salts, for example taurocholic acid, glycocholic acid, cholic acid, chenodeoxycholic acid, deoxycholate and lithocholic acid; caffeine; and/or glucocorticoids such as hydrocortisone and dexamethasone. If deoxycholate is present in the medium, it is present in a concentration of 1 to 30 µM, preferably 2 to 25 µM or 3 to 20 µM, more preferably 4 to 18 µM or 5 to 15 µM and most preferably 10 µM. If caffeine is present in the medium, it is present in a concentration of 5 to 100 µM, preferably 10 to 80 µM or 20 to 70 µM, more preferably 30 to 65 µM or 40 to 60 µM and most preferably 50 µM.

The cells are cultured in the cell culture medium comprising FGF-4 and, optionally, one or more or all of EGF, glucagon, insulin and heparin for at least seven days, and preferably no longer than 50 days, more preferably no longer than 40 days, even more preferably no longer than 35 days and most preferably they are cultured for seven to 35 days. After at least four days, preferably after at least seven days and more preferably after at least 14 days of culture in a cell culture medium containing at least FGF-4 and, optionally, one or more of EGF, insulin, glucagon and heparin, the cells have acquired at least one characteristic of human hepatocytes as described above.

The term "medium change" is intended to mean the step of removing the medium which is in contact with the cells, e.g. by aspiration, and adding fresh medium, i.e. medium which has not been in contact with the cells before. Preferably, the medium is changed at a time-point less than 1 hr, more preferably less than 45 min, even more preferably less than 30 min, and most preferably 20 min or 10 min after seeding the monocytes.

A further step of medium change may occur 18-30 h, preferably 20-28 h, more preferably 22-26 h and most preferably 24 h after seeding the monocytes.

In another preferred embodiment of the present invention the cell culture medium used in the first and/or second culturing step is serum-free, i.e. it does not contain a serum component such as horse serum, human serum or calf serum (FCS). However, the serum-free medium may contain discrete proteins or bulk protein fractions. The use of serum-free medium allows the cells to be cultured with a designed set of conditions with as few variables as possible. Furthermore, if the cells produced by the method of the present invention are intended to be used for cell therapy, the use of serum in the medium is disadvantageous, as it also bears a contamination risk.

In an even more preferred embodiment, the serum-free medium comprises albumin such as human serum albumin or bovine serum albumin. Preferably, human serum albumin is present in the medium. The human serum albumin may be obtained from suitable suppliers such as Sigma (Deisenhofen, Germany) or Baxter (Unterschleiss-heim, Germany). If present, the albumin is present in the cell culture medium in a concentration of 0.5-10%, preferably 1-8%, more preferably 1.5-5% and most preferably 2%. Preferably, the albumin is present in the serum-free medium in the first and the second culturing step of the method of the present invention.

In a further preferred embodiment of the present invention, the volume of the cell culture medium is kept low in the first and/or the second culturing step, preferably the medium volume is kept low during the whole cultivation period, i.e. in both the first and the second culturing step. Preferably, the volume of the cell culture medium is 40 to 90 $\mu l/cm^2$ or 50 to 85 $\mu l/cm^2$, more preferably it is 60 to 80 $\mu l/cm^2$ or 65 to 75 $\mu l/cm^2$ and most preferably it is 70 $\mu l/cm^2$ of the culture vessel. It has already been shown that the volume of the medium and therefore the height of the medium column above the cells influences the pericellular oxygen partial pressure (Gstraunthaler et al. (1999) Cell Physiol. Biochem. 9(3): 150-172; Wolff et al. (1993) Am. J. Physiol. 265(5): C1266-1270). It is thus assumed that the lower medium volume prevents the cells from becoming hypoxic.

After the second culturing step the cells having at least one characteristic of human hepatocytes may be harvested for further use, e.g. cell therapy. The term "harvesting the cells" is intended to mean that the cells are withdrawn from the cell culture and optionally processed for further use. The cells may e.g. be harvested by treatment with trypsin which detaches the adherent cells from the culture vessel. The cells may then be centrifuged to remove the cell culture medium. Furthermore, the cells may be washed one or more times, for example in PBS (phosphate buffered saline) or other buffered saline solutions. Alternatively, after harvesting the cells may be seeded again in a suitable medium in the same or a new culture vessel. Furthermore, for some applications such as in vitro toxicity tests the cells do not have to be harvested, but may also be used directly during or after the second culturing step.

The harvested cells may be used directly for cell therapy or in vitro toxicity tests or may be cryoconserved by freezing them at a temperature from about −196° C. to about −20° C., preferably at a temperature from about −196° C. and −80° C. Experiments have shown that the cells of the present invention maintain their characteristics after cryoconservation.

By the method of the present invention, at least $15-50 \times 10^6$, preferably at least $20-45 \times 10^6$ and more preferably $30-40 \times 10^6$ cells having at least one characteristic of human hepatocytes can be obtained from 100 ml peripheral blood within 10 to 14 days after seeding the cells.

The cells obtained by the method of the present invention, also called "cells of the present invention" or "Metaheps", can be distinguished from primary human hepatocytes (phH) by their ability to be cultured for a longer period, i.e. at least 15 days, preferably at least 17 or 20 days, more preferably at least 23 or 25 days, even more preferably at least 28 or 32 days and most preferably at least 35 days without losing their metabolic properties and their viability. The cells of the present invention are cultured for no more than 56 days, preferably no more than 52 or 49 days, more preferably no more than 45 or 42 days and most preferably no more than 38 days. In this case, the culture period is calculated from the time-point at which the treatment with FGF-4 is started.

The term "metabolic properties" is intended to mean at least one characteristic of human hepatocytes as described above, i.e. activity of enzymes such as dipeptidyl peptidase IV (DPP-IV), alanine aminotransferase (ALT), gamma glutamyl transpeptidase (γ-GT) and lactate dehydrogenase (LDH); secretion of glucose after glucagon stimulation; ability to metabolize pharmacological substances such as acetaminophen (APAP) and diclofenac; expression of albumin, α-fetoprotein, asialoglycoprotein receptors 1 and 2, carbamoyl phosphate synthetase (1) and coagulation factors I and II; expression of CYP 450 enzymes such as CYP1A2, CYP2A6, CYP2D6, CYP2P8-9, CYP2E1, CYP3A3-5, CYP2C9, CYP3A4; inducible activity of CYP 450 enzymes such as CYP1A2, CYP2C9 and CYP3A4; ability to synthesize urea after incubation with ammonium ions; ability to produce factor VII after incubation with vitamin K; ability to produce factor VIII; secretion of albumin; and expression of xenobiotic transporters such as proteins from the ABC-transporter family. Within the meaning of the present invention the metabolic properties are not lost, if any of the above properties is at least 80%, preferably at least 82% or 85%, more preferably at least 87 or 90% and most preferably 92 or 95% of the properties of the cells of the present invention cultured for seven days in the medium containing FGF-4.

The viability of the cells of the present invention can be determined by methods known in the art, e.g. by staining with trypan blue wherein the dead cells take up the dye and stain blue and the living cells do not take up the dye. Within the meaning of the present invention, the cells retain their viability, if at a specific time-point less than 20%, preferably less than 18 or 15%, more preferably less than 12% or 10% and most preferably less than 8 or 5% of the cells are dead cells.

In contrast, primary human hepatocytes maintain hepatocyte-characteristics only for up to 14 days and only when cultured under special conditions, such as serum free collagen-sandwich (Tuschl et al. (2009) Chem Biol Interact. 181(1): 124-37; G. Elaut et al. (2006) Curr. Drug Metab. 7 (6): 629-660.)

Hence, in contrast to primary human hepatocytes the cells of the present invention are suitable for the study of the long-term toxicity of substances. The term "long-term toxicity" refers to the ability of cells of the present invention to respond to treatment with a pharmacological substance such as rapamycin or APAP with the induction of cytochrome P450 enzyme expression or activity or LDH release after at least 7 days, preferably at least 10 or 14 days, more preferably at least 20 or 25 days, even more preferably at least 28 or 30 days and most preferably at least 35 days in culture.

Further, the cells of the present invention can be distinguished from immortalized cell lines such as HepG2 by their ability to undergo apoptosis, for example after treatment with an antibody activating CD95 for 24 hours. Hence, the risk that the cells of the present invention develop to tumors after transplantation into a human is low. The ability to undergo apoptosis can be measured by staining the treated cells with HOECHST stain or by measuring caspase activity in the treated cells, as described in the examples below. Another difference between the cells of the present invention and HepG2 cells is the ability of the cells of the present invention to synthesize urea after treatment with ammonia and the induction of enzymes of the cytochrome P450 system.

Finally, in contrast to the cells called "neo-hepatocytes" as described for example in Ruhnke et al. (2005) Gastroenterology 128(7): 1774-1786, Ruhnke et al. (2005) Transplantation 79(9): 1097-1103 and Riquelme et al. (2009) Differentiation 77(3): 263-276, the cells of the present invention are capable of undergoing apoptosis when treated with 500 ng/ml of the CD95 activating antibody APO for 24 hours. The term "capable of undergoing apoptosis" means that after incubation of the cells of the present invention (culture day 14) with the CD95 activating antibody APO for 24 hours the number of dead cells (measured for example by staining the cells with propidium iodide and subsequent FACS analysis) increases at least by the factor 1.5, more preferably at least by the factor 1.8, even more preferably at least by the factor 2 and most preferably at least by the factor 2.5 compared to control cells not incubated with the antibody.

It was also found by others that the "neo-hepatocytes" do not react to fatal stimulation with the death-inducing cytokines TNF-α and CD95L, although they express the corresponding receptors (doctoral thesis of Ms. Isabelle Pochic, University of Konstanz: "The Use of NeoHepatocytes for Assessment of Metabolism-Dependent Human Acute Toxicity", available at http://kops.ub.uni-konstanz.de/handle/urn:nbn:de:bsz:352-opus-57745). Hence, it was concluded that the "neo-hepatocytes" may not be useful in cell therapy.

The cells of the present invention also show higher levels of factor VII and VIII synthesis than the "neo-hepatocytes". The synthesis of factor VII in the cells of the present invention is at least 5 times, preferably at least 10 times, more preferably at least 15 times and most preferably at least 20 times higher than in the "neo-hepatocytes". The synthesis of factor VIII in the cells of the present invention is at least 3 times, preferably at least 5 times, more preferably at least 7 times and most preferably at least 10 times higher than in the "neo-hepatocytes". If the cells of the present invention and the "neo-hepatocytes" are produced in a serum-free medium, the synthesis of factor VII in the cells of the present invention is at least 20 times, preferably at least 30 times, more preferably at least 40 times and most preferably at least 50 times higher than in the "neo-hepatocytes". If the cells of the present invention and the "neo-hepatocytes" are produced in a serum-free medium, the synthesis of factor VIII in the cells of the present invention is at least 5 times, preferably at least 7 times, more preferably at least 10 times and most preferably at least 12 times higher than in the "neo-hepatocytes".

Further, in contrast to the "neo-hepatocytes" the cells of the present invention show a cytochrome activity which cannot be inhibited by treating the cells with 500 μM caffeine.

The cells of the present invention may be used in vitro to study the toxicity of substances, for example in drug screening. For example, the cells may be starved in basal medium for 8-24 h and then incubated with the basal medium containing different amounts of the substances to be tested or the corresponding vehicle for controls. For incubations up to 72 h, the medium is not changed, for longer incubation periods, medium samples are acquired and the medium is changed 3 times a week. At the end of the incubation period, medium samples are drawn and cells are lysed in the corresponding lysis buffer (e.g. Triton X100/MOPS). After lysis, protein content and enzyme activities (DPP-IV, GGT, LDH, ALT) can be determined in the lysate.

As already outlined above, the cells of the present invention may be used to investigate the acute toxicity of test compounds, but also the long-term toxicity of the test compounds, for example when incubated with the test compound for at least 14 days, more preferably at least 21 days and even more preferably at least 28 days.

The cells of the present invention may also be used in an approach called "targeted metabolomics" to investigate the mechanism of action and the metabolism, in particular of newly developed substances. In this method, metabolites are examined qualitatively and quantitatively by automated mass spectrometrical high throughput methods and functionally annotated. Based on already existing metabolic profiles conclusions with respect to metabolic pathways involved can be drawn and target structures can be identified (see, e.g., Dudley et al. (2010) Adv. Protein Chem. Struct. Biol. 80: 45-83; Koal and Deigner (2010) Curr. Mol. Med. 10(2): 216-226).

Further, the cells of the present invention may be used in metabolic phenotyping to individually characterize the CYP-dependent metabolism for developing a patient-specific treatment regimen (see, e.g., Klein et al. (2010) Front. Pharmacol. 1:1-20).

Further, the cells of the present invention may be used in cell therapy by transplanting the cells into humans suffering from acute or chronic liver failure, e.g. in the course of diseases such as drug-induced or toxic liver failure, alcohol abuse, viral hepatitis e.g. B,B/D or C, iron or copper overload or non-alcoholic fatty liver disease, cholestatic or autoimmune liver diseases, genetically inherited liver diseases and liver diseases in children. The cells may also be used as an autologous vector for gene therapy, for example by transferring RNA, of monogenetic diseases such as phenylketonuria (see, e.g., Kormann et al. (2011) Nat. Biotech. 29: 154-157).

Preferably, the cell therapy uses autologous cells, i.e. cells produced from monocytes which have been isolated from the patient to be treated with the cells of the present invention.

For cell therapy, the cells are administered as suspension in sterile PBS, 0.9% NaCl or Ringer's solution by either intrasplenic, intraportal, intrahepatic or peripheral intravenous injection or a combination thereof.

A more complete understanding of the present invention can be obtained by reference to the following specific examples which are provided herein for the purposes of illustration only and are not intended to limit the scope of the invention.

EXAMPLES

1. Production of Cells Having Characteristics of Human Hepatocytes by the Method of the Present Invention Whole blood from healthy donors was treated with heparin and separated by gradient centrifugation (400 g; room temperature; 30 minutes) using Ficoll in a 2:1 ratio of blood to Ficoll. The interphase was resuspended in ice-cold, sterile PBS in a 1:3 to 1:4 ratio of cell suspension to PBS and then centrifuged at 400 g for 5 minutes at 4° C. After the first wash, the supernatant was discarded and the cell pellet was resuspended in ice-cold, sterile PBS (for PBMCs from 50 ml whole blood, 20-30 ml of ice-cold, sterile PBS are used). If there was visible contamination by erythrocytes, this washing step is preceded by 10 min incubation in sterile hemolysis-buffer (8.29 g/l $NH_4Cl$, 1 g/l $KHCO_3$, 0.037 g/l EDTA) in the dark at room temperature. Again, after resuspension in PBS, cells were centrifuged for 5 minutes at 300 g (4° C.). Once again, the supernatant was discarded and cells were resuspended in PBS followed by a last centrifugation at 250 g for 5 minutes at 4° C.

After this final washing step, the PBS was discarded and cells were resuspended at 37° C. in a medium having the following composition:
DMEM/Ham's F12 (1:1)
10% FCS (standard conditions) or 2% human albumin (serum-free conditions)
2 mM glutamine
100 µg/ml streptomycin
1000 IE penicillin
1 ng/ml recombinant human IL-3 (R&D Systems)
100 nM adenosine (Sigma, Deisenhofen, Germany)
0.5 ng/ml recombinant human M-CSF (R&D Systems)

The cells were seeded in a density of 250.000 cells/$cm^2$ in a Petri dish which had been pre-incubated with the culture medium 30-120 minutes before seeding of the cells. If cells were seeded in 96-well plates, the outer wells were left free and just filled with cell culture medium to omit differences in temperature and partial pressures of $O_2$ and $CO_2$.

After seeding, the cells were allowed to attach for 10-30 minutes. After attachment, the medium was replaced with 70 µl fresh medium per $cm^2$ of the culture vessel. The cell culture medium was again replaced within the first 24 h of culture. After the first 24 hours of culture there was an adherent population of monocytes, characterized by small round cells with a bean-shaped nucleus. At this stage the cells showed little specific activities of DPP-IV, GGT and ALT, but there was a high expression of the monocyte marker CD14 and the pan-leukocyte-marker CD45.

After the first 24 hours, the medium was changed three times a week. Cells were cultured in the above medium for the first 4-10 days of culture.

After the cells were incubated with the medium comprising IL-3, M-CSF and adenosine, the medium was replaced with the same volume of a medium having the following composition:
DMEM/Ham's F12 (1:1)
10% FCS (standard conditions) or 2% human albumin (serum-free conditions)
2 mM glutamine
100 µg/ml streptomycin
1000 IE penicillin
3 ng/ml recombinant human FGF-4
10 ng/ml recombinant human EGF
5 nM recombinant human glucagon
0.28 IE recombinant human insulin
5 IE/ml heparin The cells were incubated in this medium for at least seven days or for the time periods indicated in the figures and figure legends. During the second culturing step, there is again an alteration in morphology, resulting in a confluent or subconfluent layer of large, mono- or multinucleated, polygonal shaped cells with an organelle rich cytoplasm, the metaheps. This morphology is observed independent of the presence or absence of serum in the culture medium.

Before experiments were performed, cells were starved by incubation with DMEM/Ham's F12 1:1 containing only L-glutamine, penicilline and streptomycin (referred to as "basal medium"). The basal medium was also used for incubations to avoid interference of medium ingredients with the assays performed. Prior to lysis, cells were washed three times with ice-cold PBS.

2. Determination of Protein Content

Protein content was determined with the bicinchoninic acid (BCA) assay (Sigma, Deisenhofen, Germany): cells were grown on culture vessels, starved for 24 h in basal medium and incubated with experimental chemicals as indicated. After removal of culture media cells were lysed in Triton X-100/MOPS and 10 µl aliquots of the lysates were incubated for 30 min at 37° C. with 200 µl of the BCA-reagent (50 parts reagent+1 part 4% $CuSO_4$). Absorbance was measured at 560 nm in a multilabel counter (Dynatech MR7000). Protein content was calculated using bovine serum albumin as a reference standard.

3. Determination of Enzyme Activities a) LDH-Activity

LDH-activity was determined spectrophotometrically by measurement of β-NAD+ resulting from the LDH catalyzed reaction of pyruvate and β-NADH to lactate and β-NAD+, using a standard protocol (Bergmeyer H. U. (Hrsg.) "Methoden der enzymatischen Analyse", 3. Aufl. 1974, Band 1, Verlag Chemie Weinheim/Bergstr.) or the Cyto Tox 96-Kit (Promega) according to the manufacturer's instructions.

b) ALT-Activity

The activity of ALT was measured by a two phase reaction consisting of the generation of pyruvate and L-glutamate from L-alanine and α-ketoglutarate by ALT and the subsequent quantification of pyruvate generation by LDH-dependent β-NAD+ formation (Schumann G et al. (2002) Clin Chem Lab Med 40(7):718-724).

Samples (cell lysates in Triton X-100/MOPS after centrifugation at 13.000 U/min at 4° C.) were incubated for 300 s at 37° C. with reaction mixture (100 mmol TRIS, 500 mmol L-alanine, 0.18 mmol β-NADH, 0.1 mmol pyridoxal-5'-phosphate, 1700 U/1 L-lactate-dehydrogenase, pH 7.15) in the absence of α-ketoglutarate. The reaction was started by addition of 15 mmol α-ketoglutarate and the decrease in β-NADH absorption was monitored for 180 s after a 90 s incubation period. Alternatively the ALT-Kit from Randox Chemicals was used according to the manufacturer's instructions.

c) Gamma-Glutamyl-Transpeptidase Activity

Gamma-glutamyl-transpeptidase activity was measured using the photometric determination of p-nitroaniline resulting from the γ-GT catalyzed reaction of L-γ-glutamyl-p-nitroanilide and glycylglycine to γ-glutamyl-glycylglycide and p-nitroaniline (Szasz G: Gamma-glutamyl-transpeptidase, in Methoden der Enzymatischen Analyse, 3rd ed., (Vol 1), edited by Bergmeyer H U, Weinheim/Bergstr., Verlag Chemie, 1974, pp 757-762).

Cells were rinsed three times with PBS, lysed with Triton-X 100, centrifuged (13.000 U/min, 10 min) and total γ-GT-activity was measured by incubating the cell lysates with 100 mM TRIS, 4 mM L-γ-glutamyl-p-nitroanilide and 50 mM glycylglycine. Absorption of p-nitroaniline was measured at 405 nm. ΔE/min was calculated from measurements at 5, 10, 15, 30 and 45 minutes.

d) DPP-IV-Activity

DPP-IV activity was measured using the photometric determination of p-nitroaniline resulting from the DPP-IV catalyzed cleavage of the chromogenic substrate Gly-L-Pro-p-nitroanilide.

Cells were lysed in Triton X-100/MOPS. After centrifugation of the lysates (13.000 U/min; 4° C.), the lysates were incubated with 0.2 mM Gly-L-Pro-pNA in 0.1 M TRIS (pH 8.0) at 37° C. and absorbance at 405 nm was read after 0, 5, 10, 15, 30 and 45 minutes to determine ΔE/min. DPP-IV activity was determined from a standard curve with p-nitroaniline and normalized to protein content as measured by the BCA-method.

4. Determination of P450 Cytochrome Activity

For CYP P450 activity measurement the P450 Glo assays (Promega) were used according to the manufacturer's instructions. Briefly, cells were starved in basal medium and incubated with different inducers (3-methylcholanthrene in concentrations from 0.1 to 10 µM, typically 1 µM for CYP1A2; 10 µM dexamethasone; 10 to 100 µM, typically 50 µM rifampicin; 5 to 10 µM, typically 10 µM phenyloin for CYP 3A4; and 50 µM rifampicin and 10 µM phenyloin for 2C9 for 24 h to 72 h). Typically, induction was performed using a 48 h incubation time. After induction, cells were rinsed three times with ice-cold PBS and incubated with basal medium containing the corresponding Luciferin-substrate according to the manufacturer's instruction and luminescence in the supernatant was measured after 30 min incubation with Luciferin detection reagent according to the manufacturer's instructions. Luminescence readings were normalized for protein content in the cell lysates as determined by the BCA-method.

To determine CYP1A2-activity using the fluorescent dye 3-cyano-7-ethoxycoumarine (Donato et al. (2004) Drug Metabolism and Disposition 32(7): 699-706), cells were treated with 3-methylcholanthrene for 48 hours and then rinsed three times with ice cold PBS, following incubation with 3-cyano-7-ethoxycoumarin (30 µM) in HEPES-buffered saline at 37° C. for 120 minutes. 75 µl of the supernatant were pipeted in an assay plate and incubated with 25 µl β-Glucuronidase/Arylsulfatase (1.5 µl/1 ml in Natriumacetat) at 37° C. for 2 h. After addition of 0.1 mM phosphate potassium buffer as quenching solution, fluorescence was measured at Excitation/Emission 408/455 nm in a plate fluorometer. Fluorescence readings were normalized to protein content as determined by the BCA-assay.

5. Determination of APAP Toxicity

Toxicity assays were performed after 24 h starvation of the cells with basal medium by incubation with different concentrations of APAP dissolved in basal medium for 24 h. LDH activity in media and lysates was determined as described above using the Cyto Tox 96 Kit from Promega and LDH release (%) was calculated by 100×(LDH-activity in media/(LDH-activity in media+LDH-activity in lysate).

6. Determination of Apoptosis a) Apoptosis by HOECHST 33342 Staining

Cells were incubated with different concentrations of anti-APO (Alexis AXXORA Biochemicals, Lörrach, Germany)/Protein A (BioVision Research Products, Mountain View, USA) for 24-48 h. After the incubation period, cells were stained with HOECHST 33342 (10 µM) for 15 minutes and analysed after three washes with PBS using a fluorescence microscope.

b) Apoptosis by Caspase-3 Measurement

Caspase-3 activity in cell lysates was determined using the chromogenic caspase-3 substrate Ac-DEVD-pNA (final concentration 40 µM) as described in Benesic et al. (2006) Kidney Blood Press Res. 29(5): 280-293. The activity was assessed using a standard curve with p-nitroaniline and normalized to protein content as measured by the BCA method.

c) Assessment of Apoptotic Cells by FACS-Analysis

To evaluate apoptosis by DNA-fragmentation, FACS-analysis of cells stained with propidium-iodide was performed. Cells were starved for 24 h with basal medium and incubated with basal medium or basal medium containing Anti-APO (Alexis AXXORA Biochemicals, Lörrach, Germany) in the indicated concentrations. After 24 h incubation, cells were detached using Accutase, centrifuged at 250 g for 5 min (4° C.) and resuspended in ice-cold PBS containing 0.2% bovine serum albumin. Under continuous agitation pure ethanol was slowly added to a final concentration of 75% ethanol in PBS/BSA. Cells were frozen at −20° C. to allow fixation overnight. Afterwards, cells were centrifuged at 400 g for 5 min (4° C.). The supernatant was discarded and cells were stained with 50 µg/l propidium iodide in PBS for at least 30 min in the dark, followed by FACS analysis. The apoptosis was assessed by evaluating the sub-G1 events.

7. Determination of Urea Synthesis

Urea synthesis was measured after 24 h starvation of the cells with basal medium, followed by 24 h incubation with different concentration of ammonium chloride (0-100 mM). The supernatants were collected and urea content was determined using the QuantiChrome™ Urea Assay Kit (Clonagen) according to the manufacturer's instructions. Urea content of the media was normalized to protein content in cell lysates as measured by the BCA method.

8. Determination of Factor VII Secretion

Factor VII secretion was measured by direct ELISA, in analogy to Esposito et al. (2000) Kidney Int. 58:123-130; Ziyadeh et al. (1990) Am. J. Physiol. 259: F704-F714). After starvation, cells were incubated for 48 h with different menadione concentrations as indicated. Media were collected and 100 µl aliquots were incubated in Immunosorb Plates (Nunc) with 200 µl Voller buffer (1.59 g $Na_2CO_3$+2.93 g $NaHCO_3$ ad 100 ml aqua bidest) overnight at 4° C. The plate was rinsed three times with 200 µl PBS/0.05% Tween-20 and blocked with 200 µl 2% BSA in PBS/0.05% Tween-20 for 2 h. Afterwards the plate was emptied and incubated with 50 µl rabbit anti-factor VII antibody (Abcam, Cambridge, Great Britain) 1:1000 in 2%-BSA-PBS/0.05% Tween-20 for 1-2 h bei 4° C. Following three washes with 200 µl PBS/0.05% Tween-20, the plate was incubated for one hour with 50 µl anti-rabbit-peroxidase-Ak 1:5000 (Santacruz, Heidelberg, Germany) in 2%-BSA-PBS/0.05% Tween-20 at room temperature in the dark. After three rinses with 200 µl PBS/0.05% Tween-20 an incubation with 100 µl HRP-substrate (0.5 mg/ml o-phenylenediamine, 11.8 mg/ml $Na_2HPO_4.2H_2O$, 7.3 mg/ml citric acid, 0.015% $H_2O_2$ in aqua bidest) in the dark for 15 and 45 minutes followed. Absorbance at 490 nm was read in a multiwell reader followed by wavelength correction (630 nm).

The absorbance was normalized for cell lysate protein content as determined by the BCA method.

9. Determination of Factor VIII Secretion

Factor VIII secretion was measured by sandwich-ELISA, in analogy to Esposito et al. (2000) Kidney Int. 58:123-130; Ziyadeh et al. (1990) Am. J. Physiol. 259: F704-F714. After starvation, cells were incubated with basal medium for 24 h. Media were collected and 100 µl aliquots were incubated for 2 h in Immunosorb Plates (Nunc) precoated with 1 µg/ml goat Anti-human factor VIII (Santacruz, Heidelberg, Germany) at room temperature. The plate was rinsed three times with 200 µl PBS/0.05% Tween-20. Afterwards the plate was emptied and incubated with 50 µl rabbit anti-factor VIII (Santacruz, Heidelberg, Germany) 1:1000 in 1%-BSA-PBS/0.05% for 1 h at room temperature. Following three washes with 200 µl PBS/0.05% Tween-20, the plate was incubated for one hour with 50 µl anti-rabbit-peroxidase-Ak 1:5000 (Santacruz) in 1%-BSA-PBS at room temperature in the dark. After three rinses with 200 µl PBS/0.05%-Tween-20 an incubation with 100 µl HRP-substrate (0.5 mg/ml o-phenylenediamine, 11.8 mg/ml $Na_2HPO_4 \cdot 2H_2O$, 7.3 mg/ml citric acid, 0.015% $H_2O_2$ in aqua bidest) in the dark for 15 and 45 minutes followed.

Absorbance at 490 nm was read in a multiwell reader followed by wavelength correction (630 nm). The absorbance was normalized for cell lysate protein content as determined by the BCA method.

10) Gene Expression Analysis in Comparison to Primary Human Hepatocytes

Gene-expression of Metaheps and primary human hepatocytes (pHH) of the same donor was analyzed by a cRNA-Microarray (Kat. Nr. OHS 401, Human Toxicology and Drug Resistance, SA Biosciences). The genes which are analyzed with this array are shown in Table 1 below.

Monocytes and hepatocytes were acquired from patients undergoing partial hepatectomy who signed informed consent for hepatocyte donation and blood withdrawal. The patients were selected in cooperation with the Human Tissue and Cell Research Foundation (HTCR, c/o BioPark, Josef-Engert-Str. 9, 93053 Regensburg).

Hepatocytes were isolated and cultured as described in Weiss et al. (2003) J. Hepatol. 38(4): 476-482). After 4 days in culture mRNA was isolated from pHH using the Array Grade total RNA isolation Kit provided by SA Biosciences according to manufacturer's instructions.

The same was performed for Metaheps on days 3, 7 and 14 of culture in FGF-4.

According to the manufacturer's instructions the mRNA samples were transcribed into biotinylated cRNA and hybridized on the Array membrane. Afterwards a chemiluminescent detection was performed using the Chemiluminescence Detection Kit provided by SA Biosciences.

Arrays were analyzed by TIGR Spotfinder software and the data were analyzed using SPSS-software. Further, Cluster analysis was performed.

11) Long-Term Toxicity in the Cells of the Present Invention

To show the suitability of the cells of the present invention for long-term toxicity studies, the cells were produced as described above and incubated for 15 days with low concentrations of acetaminophen (APAP) and diclofenac (diclo). On incubation days 1, 3, 6, 8, 10, 13 and 15 medium samples were drawn and LDH activity in media was determined using the Cytotoxicity Kit from Promega. LDH release was calculated in % as 100×(LDH in media/LDH media+LDH lysate).

Low concentrations of diclofenac show long-term toxicity in Metaheps, whereas acetaminophen exerted acute toxicity in Metaheps

12) Discussion of the Results

The presented data show the hepatocyte-like characteristics of the cells of the invention. The important findings are summarized by expression and activity of CYP P450-enzymes, such as 1A2, 2C9 and 3A4, which are also inducible using prototypic substances (e.g. ligands for arylhydrocarbon receptor (AHR), pregnane-X-receptor (PXR), constitutive androstane-receptor (CAR) and glucocorticoid receptor (GR)). The most abundant CYP P450 enzyme in the liver, CYP 2E1 could be shown indirectly by APAP-toxicity and on the protein level. Furthermore, ammonia-dependent urea-synthesis, as well as synthesis of the coagulation factors VII and VIII by ELISA could be shown. Specific enzyme activities of DPP-IV, γ-GT, and LDH are present and comparable to primary hepatocytes or hepatocyte-derived cells (such as Huh-7 or HepG2). Thus, the cells of the present invention show hepatocyte-like metabolism, gene expression, synthesis function as well as enzyme activities. Furthermore, the cells of the present invention are capable of undergoing apoptosis induced by CD95-ligation, as shown by caspase-3 activity, HOECHST-stain and FACS-analysis. This is an important feature of cells which can potentially be used for therapeutic interventions.

The observed enzyme activities, metabolism and synthesis parameters have been compared to primary human hepatocytes in culture and the cells of the present invention exhibited at least 20% of hepatocyte factor VIII-synthesis, 30% of hepatocyte CYP3A-activity as well as 70% of hepatocyte-specific enzyme activities. Further, it has been shown that the cells of the present invention are useful for long-term toxicity studies.

Compared to cells cultivated by the method of Ruhnke et al. (2005) Gastroenterology 128(7): 1774-1786 ("neo-hepatocytes"), the cells of the present invention showed about 10 to 20-fold higher factor VIII release as well as a higher CYP1A2-activity measured by 3CEC-fluorescence. Moreover, the caffeine-insensitive metabolism of 3-CEC which is mostly mediated by CYP 2C9 is nearly absent in cells cultivated by the method of Ruhnke et al. Additionally, the latter cells did not show any measurable apoptosis after 24 h CD95-ligation, another marked difference to the cells of the invention.

TABLE 1

List of genes present in the cRNA microarray

| Position | UniGene | GenBank | Symbol | Description |
|---|---|---|---|---|
| 1 | Hs.546292 | NM_002954 | RPS27A | Ribosomal protein S27a |
| 2 | Hs.546292 | NM_002954 | RPS27A | Ribosomal protein S27a |
| 3 | Hs.489033 | NM_000927 | ABCB1 | ATP-binding cassette, sub-family B (MDR/TAP), member 1 |
| 4 | Hs.287827 | NM_000443 | ABCB4 | ATP-binding cassette, sub-family B (MDR/TAP), member 4 |

TABLE 1-continued

List of genes present in the cRNA microarray

| Position | UniGene | GenBank | Symbol | Description |
|---|---|---|---|---|
| 5 | Hs.391464 | NM_004996 | ABCC1 | ATP-binding cassette, sub-family C (CFTR/MRP), member 1 |
| 6 | Hs.368243 | NM_000392 | ABCC2 | ATP-binding cassette, sub-family C (CFTR/MRP), member 2 |
| 7 | Hs.463421 | NM_003786 | ABCC3 | ATP-binding cassette, sub-family C (CFTR/MRP), member 3 |
| 8 | Hs.368563 | NM_005688 | ABCC5 | ATP-binding cassette, sub-family C (CFTR/MRP), member 5 |
| 9 | Hs.442182 | NM_001171 | ABCC6 | ATP-binding cassette, sub-family C (CFTR/MRP), member 6 |
| 10 | Hs.544577 | NM_002046 | GAPDH | Glyceraldehyde-3-phosphate dehydrogenase |
| 11 | Hs.544577 | NM_002046 | GAPDH | Glyceraldehyde-3-phosphate dehydrogenase |
| 12 | Hs.544577 | NM_002046 | GAPDH | Glyceraldehyde-3-phosphate dehydrogenase |
| 13 | Hs.546292 | NM_002954 | RPS27A | Ribosomal protein S27a |
| 14 | Hs.480218 | NM_004827 | ABCG2 | ATP-binding cassette, sub-family G (WHITE), member 2 |
| 15 | Hs.431048 | NM_005157 | ABL1 | V-abl Abelson murine leukemia viral oncogene homolog 1 |
| 16 | Hs.81934 | NM_001609 | ACADSB | Acyl-Coenzyme A dehydrogenase, short/branched chain |
| 17 | Hs.232375 | NM_000019 | ACAT1 | Acetyl-Coenzyme A acetyltransferase 1 (acetoacetyl Coenzyme A thiolase) |
| 18 | Hs.171189 | NM_001621 | AHR | Aryl hydrocarbon receptor |
| 19 | Hs.525622 | NM_005163 | AKT1 | V-akt murine thymoma viral oncogene homolog 1 |
| 20 | Hs.489365 | NM_001283 | AP1S1 | Adaptor-related protein complex 1, sigma 1 subunit |
| 21 | Hs.158932 | NM_000038 | APC | Adenomatosis polyposis coli |
| 22 | Hs.496240 | NM_000044 | AR | Androgen receptor (dihydrotestosterone receptor; testicular feminization; spinal and bulbar muscular atrophy; Kennedy disease) |
| 23 | Hs.131494 | NM_001668 | ARNT | Aryl hydrocarbon receptor nuclear translocator |
| 24 | Hs.435561 | NM_000051 | ATM | Ataxia telangiectasia mutated (includes complementation groups A, C and D) |
| 25 | Hs.377484 | NM_004323 | BAG1 | BCL2-associated athanogene |
| 26 | Hs.159428 | NM_004324 | BAX | BCL2-associated X protein |
| 27 | Hs.150749 | NM_000633 | BCL2 | B-cell CLL/lymphoma 2 |
| 28 | Hs.516966 | NM_138578 | BCL2L1 | BCL2-like 1 |
| 29 | Hs.410026 | NM_004050 | BCL2L2 | BCL2-like 2 |
| 30 | Hs.517461 | NM_004327 | BCR | Breakpoint Cluster Region |
| 31 | Hs.194143 | NM_007294 | BRCA1 | Breast cancer 1, early onset |
| 32 | Hs.34012 | NM_000059 | BRCA2 | Breast cancer 2, early onset |
| 33 | Hs.515162 | NM_004343 | CALR | Calreticulin |
| 34 | Hs.529890 | NM_001746 | CANX | Calnexin |
| 35 | Hs.2490 | NM_033292 | CASP1 | Caspase 1, apoptosis-related cysteine protease (interleukin 1, beta, convertase) |
| 36 | Hs.5353 | NM_001230 | CASP10 | Caspase 10, apoptosis-related cysteine protease |
| 37 | Hs.369736 | NM_001228 | CASP8 | Caspase 8, apoptosis-related cysteine protease |
| 38 | Hs.502302 | NM_001752 | CAT | Catalase |
| 39 | Hs.57907 | NM_002989 | CCL21 | Chemokine (C-C motif) ligand 21 |
| 40 | Hs.514107 | NM_002983 | CCL3 | Chemokine (C-C motif) ligand 3 |
| 41 | Hs.75703 | NM_002984 | CCL4 | Chemokine (C-C motif) ligand 4 |
| 42 | Hs.430646 | NM_005190 | CCNC | Cyclin C |
| 43 | Hs.523852 | NM_053056 | CCND1 | Cyclin D1 (PRAD1: parathyroid adenomatosis 1) |
| 44 | Hs.244723 | NM_001238 | CCNE1 | Cyclin E1 |
| 45 | Hs.79101 | NM_004060 | CCNG1 | Cyclin G1 |
| 46 | Hs.189772 | NM_006431 | CCT2 | Chaperonin containing TCP1, subunit 2 (beta) |
| 47 | Hs.491494 | NM_005998 | CCT3 | Chaperonin containing TCP1, subunit 3 (gamma) |
| 48 | Hs.421509 | NM_006430 | CCT4 | Chaperonin containing TCP1, subunit 4 (delta) |
| 49 | Hs.1600 | NM_012073 | CCT5 | Chaperonin containing TCP1, subunit 5 (epsilon) |
| 50 | Hs.368149 | NM_006429 | CCT7 | Chaperonin containing TCP1, subunit 7 (eta) |
| 51 | Hs.125113 | NM_006585 | CCT8 | Chaperonin containing TCP1, subunit 8 (theta) |
| 52 | Hs.19192 | NM_001798 | CDK2 | Cyclin-dependent kinase 2 |
| 53 | Hs.95577 | NM_000075 | CDK4 | Cyclin-dependent kinase 4 |
| 54 | Hs.370771 | NM_000389 | CDKN1A | Cyclin-dependent kinase inhibitor 1A (p21, Cip1) |
| 55 | Hs.238990 | NM_004064 | CDKN1B | Cyclin-dependent kinase inhibitor 1B (p27, Kip1) |
| 56 | Hs.512599 | NM_058195 | CDKN2A | Cyclin-dependent kinase inhibitor 2A (melanoma, p16, inhibits CDK4) |
| 57 | Hs.435051 | NM_001800 | CDKN2D | Cyclin-dependent kinase inhibitor 2D (p19, inhibits CDK4) |
| 58 | Hs.535486 | NM_016280 | CES4 | Carboxylesterase 4-like |
| 59 | Hs.302002 | NM_020985 | CHAT | Choline acetyltransferase |
| 60 | Hs.291363 | NM_007194 | CHEK2 | CHK2 checkpoint homolog (S. pombe) |
| 61 | Hs.104576 | NM_003654 | CHST1 | Carbohydrate (keratan sulfate Gal-6) sulfotransferase 1 |
| 62 | Hs.516370 | NM_004854 | CHST10 | Carbohydrate sulfotransferase 10 |
| 63 | Hs.8786 | NM_004267 | CHST2 | Carbohydrate (N-acetylglucosamine-6-O) sulfotransferase 2 |
| 64 | Hs.158304 | NM_004273 | CHST3 | Carbohydrate (chondroitin 6) sulfotransferase 3 |
| 65 | Hs.251383 | NM_005769 | CHST4 | Carbohydrate (N- |

TABLE 1-continued

List of genes present in the cRNA microarray

| Position | UniGene | GenBank | Symbol | Description |
|---|---|---|---|---|
| 66 | Hs.156784 | NM_012126 | CHST5 | Carbohydrate (N-acetylglucosamine 6-O) sulfotransferase 4 |
| 67 | Hs.157439 | NM_021615 | CHST6 | Carbohydrate (N-acetylglucosamine 6-O) sulfotransferase 5 |
| 68 | Hs.138155 | NM_019886 | CHST7 | Carbohydrate (N-acetylglucosamine 6-O) sulfotransferase 6 |
| 69 | Hs.165724 | NM_022467 | CHST8 | Carbohydrate (N-acetylglucosamine 6-O) sulfotransferase 7 |
| 70 | Hs.436657 | NM_001831 | CLU | Carbohydrate (N-acetylgalactosamine 4-O) sulfotransferase 8 |
|  |  |  |  | Clusterin (complement lysis inhibitor, SP-40,40, sulfated glycoprotein 2, testosterone-repressed prostate |
| 71 | Hs.370408 | NM_000754 | COMT | Catechol-O-methyltransferase |
| 72 | Hs.346950 | NM_004378 | CRABP1 | Cellular retinoic acid binding protein 1 |
| 73 | Hs.12068 | NM_000755 | Crat | Carnitine acetyltransferase |
| 74 | Hs.184085 | NM_000394 | CRYAA | Crystallin, alpha A |
| 75 | Hs.408767 | NM_001885 | CRYAB | Crystallin, alpha B |
| 76 | Hs.1349 | NM_000758 | CSF2 | Colony stimulating factor 2 (granulocyte-macrophage) |
| 77 | Hs.473087 | NM_001905 | CTPS | CTP synthase |
| 78 | Hs.413924 | NM_001565 | CXCL10 | Chemokine (C—X—C motif) ligand 10 |
| 79 | Hs.303980 | NM_000781 | CYP11A1 | Cytochrome P450, family 11, subfamily A, polypeptide 1 |
| 80 | Hs.511880 | NM_000498 | CYP11B2 | Cytochrome P450, family 11, subfamily B, polypeptide 2 |
| 81 | Hs.72912 | NM_000499 | CYP1A1 | Cytochrome P450, family 1, subfamily A, polypeptide 1 |
| 82 | Hs.1361 | NM_000761 | CYP1A2 | Cytochrome P450, family 1, subfamily A, polypeptide 2 |
| 83 | Hs.154654 | NM_000104 | CYP1B1 | Cytochrome P450, family 1, subfamily B, polypeptide 1 |
| 84 | Hs.446065 | NM_020674 | CYP20A1 | Cytochrome P450, family 20, subfamily A, polypeptide 1 |
| 85 | Hs.89663 | NM_000782 | CYP24A1 | Cytochrome P450, family 24, subfamily A, polypeptide 1 |
| 86 | Hs.91546 | NM_019885 | CYP26B1 | Cytochrome P450, family 26, subfamily B, polypeptide 1 |
| 87 | Hs.439056 | NM_000762 | CYP2A6 | Cytochrome P450, family 2, subfamily A, polypeptide 6 |
| 88 | Hs.1360 | NM_000767 | CYP2B6 | Cytochrome P450, family 2, subfamily B, polypeptide 6 |
| 89 | Hs.282871 | NM_000770 | CYP2C8 | Cytochrome P450, family 2, subfamily C, polypeptide 8 |
| 90 | Hs.282624 | NM_000771 | CYP2C9 | Cytochrome P450, family 2, subfamily C, polypeptide 9 |
| 91 | Hs.534311 | NM_000106 | CYP2D6 | Cytochrome P450, family 2, subfamily D, polypeptide 6 |
| 92 | Hs.12907 | NM_000773 | CYP2E1 | Cytochrome P450, family 2, subfamily E, polypeptide 1 |
| 93 | Hs.363140 | NM_000774 | CYP2F1 | Cytochrome P450, family 2, subfamily F, polypeptide 1 |
| 94 | Hs.442527 | NM_017460 | CYP3A4 | Cytochrome P450, family 3, subfamily A, polypeptide 4 |
| 95 | Hs.150276 | NM_000777 | CYP3A5 | Cytochrome P450, family 3, subfamily A, polypeptide 43 |
| 96 | Hs.1645 | NM_000778 | CYP4A11 | Cytochrome P450, family 4, subfamily A, polypeptide 11 |
| 97 | Hs.436317 | NM_000779 | CYP4B1 | Cytochrome P450, family 4, subfamily B, polypeptide 1 |
| 98 | Hs.106242 | NM_000896 | CYP4F3 | Cytochrome P450, family 4, subfamily F, polypeptide 3 |
| 99 | Hs.1644 | NM_000780 | CYP7A1 | Cytochrome P450, family 7, subfamily A, polypeptide 1 |
| 100 | Hs.491869 | NM_004820 | CYP7B1 | Cytochrome P450, family 7, subfamily B, polypeptide 1 |
| 101 | Hs.447793 | NM_004391 | CYP8B1 | Cytochrome P450, family 8, subfamily B, polypeptide 1 |
| 102 | Hs.505777 | NM_004083 | DDIT3 | DNA-damage-inducible transcript 3 |
| 103 | Hs.83765 | NM_000791 | DHFR | Dihydrofolate reductase |
| 104 | Hs.517666 | NM_007326 | DIA1 | Diaphorase (NADH) (cytochrome b-5 reductase) |
| 105 | Hs.335551 | NM_001931 | DLAT | Dihydrolipoamide S-acetyltransferase (E2 component of pyruvate dehydrogenase complex) |
| 106 | Hs.445203 | NM_001539 | DNAJA1 | DnaJ (Hsp40) homolog, subfamily A, member 1 |
| 107 | Hs.368078 | NM_005880 | DNAJA2 | DnaJ (Hsp40) homolog, subfamily A, member 2 |
| 108 | Hs.459779 | NM_005147 | DNAJA3 | DnaJ (Hsp40) homolog, subfamily A, member 3 |
| 109 | Hs.513053 | NM_018602 | DNAJA4 | DnaJ (Hsp40) homolog, subfamily A, member 4 |
| 110 | Hs.515210 | NM_006145 | DNAJB1 | DnaJ (Hsp40) homolog, subfamily B, member 1 |
| 111 | Hs.317192 | NM_016306 | DNAJB11 | DnaJ (Hsp40) homolog, subfamily B, member 11 |
| 112 | Hs.77768 | NM_006736 | DNAJB2 | DnaJ (Hsp40) homolog, subfamily B, member 2 |
| 113 | Hs.380282 | NM_007034 | DNAJB4 | DnaJ (Hsp40) homolog, subfamily B, member 4 |
| 114 | Hs.237506 | NM_012266 | DNAJB5 | DnaJ (Hsp40) homolog, subfamily B, member 5 |
| 115 | Hs.6790 | NM_012328 | DNAJB9 | DnaJ (Hsp40) homolog, subfamily B, member 9 |
| 116 | Hs.172847 | NM_005528 | DNAJC4 | DnaJ (Hsp40) homolog, subfamily C, member 4 |
| 117 | Hs.164419 | NM_025219 | DNAJC5 | DnaJ (Hsp40) homolog, subfamily C, member 5 |
| 118 | Hs.500156 | NM_003315 | DNAJC7 | DnaJ (Hsp40) homolog, subfamily C, member 7 |
| 119 | Hs.433540 | NM_014280 | DNAJC8 | DnaJ (Hsp40) homolog, subfamily C, member 8 |
| 120 | Hs.335034 | NM_000110 | DPYD | Dihydropyrimidine dehydrogenase |
| 121 | Hs.96055 | NM_005225 | E2F1 | E2F transcription factor 1 |
| 122 | Hs.488293 | NM_005228 | EGFR | Epidermal growth factor receptor |

TABLE 1-continued

List of genes present in the cRNA microarray

| Position | UniGene | GenBank | Symbol | Description |
|---|---|---|---|---|
| | | | | (erythroblastic leukemia viral (v-erb-b) oncogene homolog, avian) |
| 123 | Hs.326035 | NM_001964 | EGR1 | Early growth response 1 |
| 124 | Hs.181128 | NM_005229 | ELK1 | ELK1, member of ETS oncogene family |
| 125 | Hs.89649 | NM_000120 | EPHX1 | Hypothetical gene supported by AK124699 |
| 126 | Hs.212088 | NM_001979 | EPHX2 | Epoxide hydrolase 2, cytoplasmic |
| 127 | Hs.446352 | NM_004448 | ERBB2 | V-erb-b2 erythroblastic leukemia viral oncogene homolog 2, neuro/glioblastoma derived oncogene homolog |
| 128 | Hs.118681 | NM_001982 | ERBB3 | V-erb-b2 erythroblastic leukemia viral oncogene homolog 3 (avian) |
| 129 | Hs.390729 | NM_005235 | ERBB4 | V-erb-a erythroblastic leukemia viral oncogene homolog 4 (avian) |
| 130 | Hs.435981 | NM_001983 | ERCC1 | Excision repair cross-complementing rodent repair deficiency, complementation group 1 (includes overlapping antisense sequence) |
| 131 | Hs.469872 | NM_000122 | ERCC3 | Excision repair cross-complementing rodent repair deficiency, complementation group 3 (xeroderma pigmentosum group B complementing) |
| 132 | Hs.208124 | NM_000125 | ESR1 | Estrogen receptor 1 |
| 133 | Hs.443150 | NM_001437 | ESR2 | Estrogen receptor 2 (ER beta) |
| 134 | Hs.284244 | NM_002006 | FGF2 | Fibroblast growth factor 2 (basic) |
| 135 | Hs.1424 | NM_002021 | FMO1 | Flavin containing monooxygenase 1 |
| 136 | Hs.386502 | NM_002022 | FMO4 | Flavin containing monooxygenase 4 |
| 137 | Hs.303476 | NM_001461 | FMO5 | Flavin containing monooxygenase 5 |
| 138 | Hs.25647 | NM_005252 | FOS | V-fos FBJ murine osteosarcoma viral oncogene homolog |
| 139 | Hs.80409 | NM_001924 | GADD45A | Growth arrest and DNA-damage-inducible, alpha |
| 140 | Hs.110571 | NM_015675 | GADD45B | Growth arrest and DNA-damage-inducible, beta |
| 141 | Hs.17958 | NM_004861 | GAL3ST1 | Galactose-3-O-sulfotransferase 1 |
| 142 | Hs.515258 | NM_004864 | GDF15 | Growth differentiation factor 15 |
| 143 | Hs.76686 | NM_000581 | GPX1 | Glutathione peroxidase 1 |
| 144 | Hs.2704 | NM_002083 | GPX2 | Glutathione peroxixdase 2 (gastrointestinal) |
| 145 | Hs.271510 | NM_000637 | GSR | Glutathione reductase |
| 146 | Hs.102484 | NM_000847 | GSTA3 | Glutathione S-transferase A3 |
| 147 | Hs.485557 | NM_001512 | GSTA4 | Glutathione S-transferase A4 |
| 148 | Hs.301961 | NM_000561 | GSTM1 | Glutathione S-transferase M1 |
| 149 | Hs.279837 | NM_000848 | GSTM2 | Glutathione S-transferase M2 (muscle) |
| 150 | Hs.2006 | NM_000849 | GSTM3 | Glutathione S-transferase M3 (brain) |
| 151 | Hs.75652 | NM_000851 | GSTM5 | Glutathione S-transferase M5 |
| 152 | Hs.190028 | NM_004832 | GSTO1 | Glutathione S-transferase omega 1 |
| 153 | Hs.523836 | NM_000852 | GSTP1 | Glutathione S-transferase pi |
| 154 | Hs.268573 | NM_000853 | GSTT1 | Glutathione S-transferase theta 1 |
| 155 | Hs.1581 | NM_000854 | GSTT2 | Glutathione S-transferase theta 2 |
| 156 | Hs.470611 | NM_003642 | HAT1 | Histone acetyltransferase 1 |
| 157 | Hs.509554 | NM_001530 | HIF1A | Hypoxia-inducible factor 1, alpha subunit (basic helix-loop-helix transcription factor) |
| 158 | Hs.517581 | NM_002133 | HMOX1 | Heme oxygenase (decycling) 1 |
| 159 | Hs.284279 | NM_002134 | HMOX2 | Heme oxygenase (decycling) 2 |
| 160 | Hs.42151 | NM_006895 | HNMT | Histamine N-methyltransferase |
| 161 | Hs.121443 | NM_139211 | HOP | Homeodomain-only protein |
| 162 | Hs.530227 | NM_005526 | HSF1 | Heat shock transcription factor 1 |
| 163 | Hs.520028 | NM_005345 | HSPA1A | Heat shock 70 kDa protein 1A |
| 164 | Hs.80288 | NM_005527 | HSPA1L | Heat shock 70 kDa protein 1-like |
| 165 | Hs.432648 | NM_021979 | HSPA2 | Heat shock 70 kDa protein 2 |
| 166 | Hs.90093 | NM_002154 | HSPA4 | Heat shock 70 kDa protein 4 |
| 167 | Hs.3268 | NM_002155 | HSPA6 | Heat shock 70 kDa protein 6 (HSP70B') |
| 168 | Hs.180414 | NM_006597 | HSPA8 | Heat shock 70 kDa protein 8 |
| 169 | Hs.184233 | NM_004134 | HSPA9B | Heat shock 70 kDa protein 9B (mortalin-2) |
| 170 | Hs.520973 | NM_001540 | HSPB1 | Heat shock 27 kDa protein 1 |
| 171 | Hs.78846 | NM_001541 | HSPB2 | Heat shock 27 kDa protein 2 |
| 172 | Hs.41707 | NM_006308 | HSPB3 | Heat shock 27 kDa protein 3 |
| 173 | Hs.525600 | NM_005348 | HSPCA | Heat shock 90 kDa protein 1, alpha |
| 174 | Hs.509736 | NM_007355 | HSPCB | Heat shock 90 kDa protein 1, beta |
| 175 | Hs.471014 | NM_002156 | HSPD1 | Heat shock 60 kDa protein 1 (chaperonin) |
| 176 | Hs.1197 | NM_002157 | HSPE1 | Heat shock 10 kDa protein 1 (chaperonin 10) |
| 177 | Hs.36927 | NM_006644 | HSPH1 | Heat shock 105 kDa/110 kDa protein 1 |
| 178 | Hs.277704 | NM_006389 | HYOU1 | Hypoxia up-regulated 1 |
| 179 | Hs.20573 | NM_000875 | IGF1R | Insulin-like growth factor 1 receptor |
| 180 | Hs.487062 | NM_000876 | IGF2R | Insulin-like growth factor 2 receptor |
| 181 | Hs.274313 | NM_002178 | GFBP6 | IInsulin-like growth factor binding protein 6 |
| 182 | Hs.83077 | NM_001562 | IL18 | Interleukin 18 (interferon-gamma-inducing factor) |
| 183 | Hs.1722 | NM_000575 | IL1A | Interleukin 1, alpha |
| 184 | Hs.126256 | NM_000576 | IL1B | Interleukin 1, beta |
| 185 | Hs.512234 | NM_000600 | IL6 | Interleukin 6 (interferon-beta 2) |
| 186 | Hs.36 | NM_000595 | LTA | Lymphotoxin alpha (TNF superfamily, member 1) |
| 187 | Hs.183109 | NM_000240 | MAOA | Monoamine oxidase A |

TABLE 1-continued

List of genes present in the cRNA microarray

| Position | UniGene | GenBank | Symbol | Description |
|---|---|---|---|---|
| 188 | Hs.46732 | NM_000898 | MAOB | Monoamine oxidase B |
| 189 | Hs.369849 | NM_002392 | MDM2 | Mdm2, transformed 3T3 cell double minute 2, p53 binding protein (mouse) |
| 190 | Hs.132966 | NM_000245 | MET | Met proto-oncogene (hepatocyte growth factor receptor) |
| 191 | Hs.501522 | NM_002412 | MGMT | O-6-methylguanine-DNA methyltransferase |
| 192 | Hs.389700 | NM_020300 | MGST1 | Microsomal glutathione S-transferase 1 |
| 193 | Hs.81874 | NM_002413 | MGST2 | Microsomal glutathione S-transferase 2 |
| 194 | Hs.191734 | NM_004528 | MGST3 | Microsomal glutathione S-transferase 3 |
| 195 | Hs.407995 | NM_002415 | MIF | Macrophage migration inhibitory factor (glycosylation-inhibiting factor) |
| 196 | Hs.195364 | NM_000249 | MLH1 | MutL homolog 1, colon cancer, nonpolyposis type 2 (*E. coli*) |
| 197 | Hs.156519 | NM_000251 | MSH2 | MutS homolog 2, colon cancer, nonpolyposis type 1 (*E. coli*) |
| 198 | Hs.374950 | NM_005952 | MT1X | Metallothionein 1X |
| 199 | Hs.73133 | NM_005954 | MT3 | Metallothionein 3 (growth inhibitory factor (neurotrophic)) |
| 200 | Hs.513488 | NM_017458 | MVP | Major vault protein |
| 201 | Hs.202453 | NM_002467 | MYC | V-myc myelocytomatosis viral oncogene homolog (avian) |
| 202 | Hs.21907 | NM_007067 | MYST2 | MYST histone acetyltransferase 2 |
| 203 | Hs.35758 | NM_012330 | MYST4 | MYST histone acetyltransferase (monocytic leukemia) 4 |
| 204 | Hs.155956 | NM_000662 | NAT1 | N-acetyltransferase 1 (arylamine N-acetyltransferase) |
| 205 | Hs.2 | NM_000015 | NAT2 | N-acetyltransferase 2 (arylamine N-acetyltransferase) |
| 206 | Hs.368783 | NM_016100 | NAT5 | N-acetyltransferase 5 (ARD1 homolog, *S. cerevisiae*) |
| 207 | Hs.14637 | NM_003960 | NAT8 | -acetyltransferase 8 (camello like) |
| 208 | Hs.431926 | NM_003998 | NFKB1 | Nuclear factor of kappa light polypeptide gene enhancer in B-cells 1 (p105) |
| 209 | Hs.73090 | NM_002502 | NFKB2 | Nuclear factor of kappa light polypeptide gene enhancer in B-cells 2 (p49/p100) |
| 210 | Hs.81328 | NM_020529 | NFKBIA | Nuclear factor of kappa light polypeptide gene enhancer in B-cells inhibitor, alpha |
| 211 | Hs.9731 | NM_002503 | NFKBIB | Nuclear factor of kappa light polypeptide gene enhancer in B-cells inhibitor, beta |
| 212 | Hs.503911 | NM_006169 | NNMT | Nicotinamide N-methyltransferase |
| 213 | Hs.462525 | NM_153292 | NOS2A | Nitric oxide synthase 2A (inducible, hepatocytes) |
| 214 | Hs.406515 | NM_000903 | NQO1 | NAD(P)H dehydrogenase, quinone 1 |
| 215 | Hs.7303 | NM_022002 | NR1I2 | Nuclear receptor subfamily 1, group I, member 2 |
| 216 | Hs.349642 | NM_005122 | NR1I3 | Nuclear receptor subfamily 1, group I, member 3 |
| 217 | Hs.534331 | NM_002452 | NUDT1 | Nudix (nucleoside diphosphate linked moiety X)-type motif 1 |
| 218 | Hs.147433 | NM_182649 | PCNA | Proliferating cell nuclear antigen |
| 219 | Hs.440967 | NM_000940 | PON3 | Paraoxonase 3 |
| 220 | Hs.354056 | NM_000941 | POR | P450 (cytochrome) oxidoreductase |
| 221 | Hs.485196 | NM_006238 | PPARD | Peroxisome proliferative activated receptor, delta |
| 222 | Hs.162646 | NM_015869 | PPARG | Peroxisome proliferative activated receptor, gamma |
| 223 | Hs.527078 | NM_013261 | PPARGC1A | Peroxisome proliferative activated receptor, gamma, coactivator 1 |
| 224 | Hs.180909 | NM_002574 | PRDX1 | Peroxiredoxin 1 |
| 225 | Hs.432121 | NM_005809 | PRDX2 | Peroxiredoxin 2 |
| 226 | Hs.201978 | NM_000962 | PTGS1 | Prostaglandin-endoperoxide synthase 1 (prostaglandin G/H synthase and cyclooxygenase) |
| 227 | Hs.196384 | NM_000963 | PTGS2 | Prostaglandin-endoperoxide synthase 2 (prostaglandin G/H synthase and cyclooxygenase) |
| 228 | Hs.440960 | NM_005053 | RAD23A | RAD23 homolog A (*S. cerevisiae*) |
| 229 | Hs.242635 | NM_005732 | RAD50 | RAD50 homolog (*S. cerevisiae*) |
| 230 | Hs.446554 | NM_002875 | RAD51 | RAD51 homolog (RecA homolog, *E. coli*) (*S. cerevisiae*) |
| 231 | Hs.535499 | NM_000964 | RARA | Retinoic acid receptor, alpha |
| 232 | Hs.436538 | NM_000965 | RARB | Retinoic acid receptor, beta |
| 233 | Hs.1497 | NM_000966 | RARG | Retinoic acid receptor, gamma |
| 234 | Hs.408528 | NM_000321 | RB1 | Retinoblastoma 1 (including osteosarcoma) |
| 235 | Hs.307905 | NM_006509 | RELB | V-rel reticuloendotheliosis viral oncogene homolog B, nuclear factor of kappa light polypeptidgene enhancer in B-cells 3 (avian) |
| 236 | Hs.20084 | NM_002957 | RXRA | Retinoid X receptor, alpha |
| 237 | Hs.388034 | NM_021976 | RXRB | Retinoid X receptor, beta |
| 238 | Hs.26550 | NM_006917 | RXRG | Retinoid X receptor, gamma |
| 239 | Hs.23978 | NM_002967 | SAFB | Scaffold attachment factor B |
| 240 | Hs.241579 | NM_001235 | SERPINH1 | Serine (or cysteine) proteinase inhibitor, clade H (heat shock protein 47), member 1, (collagen binding |

TABLE 1-continued

List of genes present in the cRNA microarray

| Position | UniGene | GenBank | Symbol | Description |
|---|---|---|---|---|
| 241 | Hs.443914 | NM_000454 | SOD1 | Superoxide dismutase 1, soluble (amyotrophic lateral sclerosis 1 (adult)) protein 1) |
| 242 | Hs.487046 | NM_000636 | SOD2 | Superoxide dismutase 2, mitochondrial |
| 243 | Hs.458345 | NM_000348 | SRD5A2 | Steroid-5-alpha-reductase, alpha polypeptide 2 (3-oxo-5 alpha-steroid delta4-dehydrogenase alpha 2) |
| 244 | Hs.546303 | NM_003932 | ST13 | Suppression of tumorigenicity 13 (colon carcinoma) (Hsp70 interacting protein) |
| 245 | Hs.142 | NM_001055 | SULT1A | Sulfotransferase family, cytosolic, 1A, phenol-preferring, member 1 |
| 246 | Hs.129742 | NM_014465 | SULT1B1 | Sulfotransferase family, cytosolic, 1B, member 1 |
| 247 | Hs.436123 | NM_001056 | SULT1C1 | Sulfotransferase family, cytosolic, 1C, member 1 |
| 248 | Hs.312644 | NM_006588 | SULT1C2 | Sulfotransferase family, cytosolic, 1C, member 2 |
| 249 | Hs.479898 | NM_005420 | SULT1E1 | Sulfotransferase family 1E, estrogen-preferring, member 1 |
| 250 | Hs.515835 | NM_003167 | SULT2A1 | Sulfotransferase family, cytosolic, 2A, o dehydrepiandrosterone (DHEA)-preferring, member 1 |
| 251 | Hs.369331 | NM_004605 | SULT2B1 | Sulfotransferase family, cytosolic, 2B, member 1 |
| 252 | Hs.189810 | NM_014351 | SULT4A1 | Sulfotransferase family 4A, member 1 |
| 253 | Hs.509736 | NM_007355 | HSPCB | Heat shock 90 kDa protein 1, beta |
| 254 | Hs.520757 | NM_001061 | TBXAS1 | Thromboxane A synthase 1 (platelet, cytochrome P450, family 5, subfamily A) |
| 255 | Hs.487054 | NM_030752 | TCP1 | T-complex 1 |
| 256 | Hs.241570 | NM_000594 | TNF | Tumor necrosis factor (TNF superfamily, member 2) |
| 257 | Hs.204044 | NM_003839 | TNFRSF11A | Tumor necrosis factor receptor superfamily, member 11a, activator of NFKB |
| 258 | Hs.279594 | NM_001065 | TNFRSF1A | Tumor necrosis factor receptor superfamily, member 1A |
| 259 | Hs.478275 | NM_003810 | TNFSF10 | Tumor necrosis factor (ligand) superfamily, member 10 |
| 260 | Hs.2007 | NM_000639 | FASLG | Fas ligand (TNF superfamily, member 6) |
| 261 | Hs.472737 | NM_003286 | TOP1 | Topoisomerase (DNA) I |
| 262 | Hs.408312 | NM_000546 | TP53 | Tumor protein p53 (Li-Fraumeni syndrome) |
| 263 | N/A | N/A | Pol1 | *Escherichia coli* K12 MG1655 section 351 of 400 of the complete genome |
| 264 | N/A | L08752 | PUC18 | PUC18 Plasmid DNA |
| 265 | Hs.534255 | NM_004048 | B2M | Beta-2-microglobulin |
| 266 | Blank | Blank | Blank | |
| 267 | Blank | Blank | Blank | |
| 268 | Hs.444319 | NM_000367 | TPMT | Thiopurine S-methyltransferase |
| 269 | Hs.421194 | NM_003596 | TPST1 | Tyrosylprotein sulfotransferase 1 |
| 270 | Hs.438649 | NM_003595 | TPST2 | Tyrosylprotein sulfotransferase 2 |
| 271 | Hs.192374 | NM_003299 | TRA1 | Tumor rejection antigen (gp96) 1 |
| 272 | N/A | X03205 | 18SrRNA | Human 18S ribosomal RNA |
| 273 | N/A | N/A | AS1R3 | Artificial Sequence 1 Related 3 (70% identity) (43/60) |
| 274 | N/A | N/A | AS1R2 | Artificial Sequence 1 Related 2 (80% identity) (48/60) |
| 275 | N/A | N/A | AS1R1 | Artificial Sequence 1 Related 1 (90% identity) (56/60) |
| 276 | N/A | N/A | AS1 | Artificial Sequence 1 |
| 277 | Hs.534255 | NM_004048 | B2M | Beta-2-microglobulin |
| 278 | Hs.534255 | NM_004048 | B2M | Beta-2-microglobulin |
| 279 | Hs.520640 | NM_001101 | ACTB | Actin, beta |
| 280 | Hs.460996 | NM_003789 | TRADD | TNFRSF1A-associated via death domain |
| 281 | Hs.369762 | NM_001071 | TYMS | Thymidylate synthetase |
| 282 | Hs.250 | NM_000379 | XDH | Xanthine dehydrogenase |
| 283 | Hs.129727 | NM_005431 | XRCC2 | -ray repair complementing defective repair in Chinese hamster cells 2 |
| 284 | N/A | N/A | BAS2C | Biotinylated Artificial Sequence 2 Complementary sequence |
| 285 | N/A | N/A | BAS2C | Biotinylated Artificial Sequence 2 Complementary sequence |
| 286 | N/A | N/A | BAS2C | Biotinylated Artificial Sequence 2 Complementary sequence |
| 287 | N/A | N/A | BAS2C | Biotinylated Artificial Sequence 2 Complementary sequence |
| 288 | N/A | N/A | BAS2C | Biotinylated Artificial Sequence 2 Complementary sequence |

The invention claimed is:

1. A method for producing cells having at least one characteristic of human hepatocytes, said method comprising the steps of:
   (a) seeding human monocytes in a culture vessel in a cell culture medium;
   (b) culturing the monocytes in a cell culture medium comprising interleukin 3 (IL-3) and adenosine; and
   (c) culturing the cells subsequent to step (b) in a cell culture medium comprising fibroblast growth factor 4 (FGF-4), wherein the cell culture medium comprising FGF-4 does not comprise adenosine.

2. The method of claim 1, wherein the cell culture medium in step (b) further comprises macrophage-colony stimulating factor (M-CSF).

3. The method of claim 1, wherein the adenosine is present in the cell culture medium of step (b) in a concentration of 10 to 300 nM.

4. The method of claim 1, wherein the cell culture medium in step (c) further comprises at least one compound selected from the group consisting of epidermal growth factor (EGF), glucagon, insulin and heparin.

5. The method of claim 4, wherein the cell culture medium in step (c) comprises EGF, glucagon, insulin and heparin.

6. The method of claim 1, wherein the cell culture medium in steps (a), (b) and/or (c) is serum-free.

7. The method of claim 6, wherein the cell culture medium in steps (a), (b) and/or (c) comprises albumin.

8. The method of claim 1, further comprising a step of changing the cell culture medium at a time-point less than one hour after seeding the human monocytes.

9. The method of claim 1, wherein in step (b) and/or (c) the cell culture medium volume is 40 to 90 µl/cm$^2$ of the culture vessel.

10. The method of claim 1, wherein in step (b) the cells are cultured for at least four days.

11. The method of claim 1, wherein in step (c) the cells are cultured for at least seven days.

12. Cells having at least one characteristic of human hepatocytes obtainable by the method of claim 1, wherein the cells can be kept in culture for at least 15 days.

13. Cells according to claim 12, wherein the cells are capable of undergoing apoptosis when incubated with a CD95-ligating antibody for 24 hours.

14. A method of using the cells of claim 12 in in vitro toxicity studies.

* * * * *